.United States Patent [19]

Forte et al.

[11] 4,404,273
[45] Sep. 13, 1983

[54] PROCESS FOR THE PRODUCTION OF PHOTOGRAPHIC COLOR IMAGES BY THE SILVER DYE BLEACH PROCESS

[75] Inventors: Eddy Forte, Lausanne; Mario Fryberg, Praroman-le-Mouret; Gerald Jan, Fribourg, all of Switzerland

[73] Assignee: Ciba-Geigy AG, Basel, Switzerland

[21] Appl. No.: 326,786

[22] Filed: Dec. 2, 1981

[30] Foreign Application Priority Data

Dec. 15, 1980 [CH] Switzerland .......................... 9248/80

[51] Int. Cl.$^3$ .......................... G03C 7/00; G03C 1/76; G03C 1/40
[52] U.S. Cl. .................................. 430/377; 430/376; 430/543; 430/546; 430/505; 430/393; 430/431; 430/460; 430/461; 430/462
[58] Field of Search ............... 430/543, 546, 505, 393, 430/376, 431, 377, 460, 461, 462

[56] References Cited

U.S. PATENT DOCUMENTS 2,071,688  2/1937  Gaspar .................................. 430/375
2,653,874  9/1953  Dreyfuss .............................. 430/393

Primary Examiner—Won H. Louie, Jr.
Attorney, Agent, or Firm—Joseph G. Kolodny

[57] ABSTRACT

A process for the production of photographic color images by the silver dye bleach process, by exposure, silver development, dye formation, dye bleach, silver bleach and fixing of a photographic material which, in a light-sensitive silver halide emulsion layer or in an adjacent layer, contains, dispersed in oil, an oil-soluble triazene of the formula

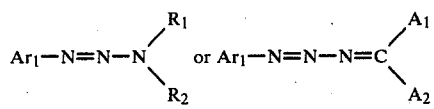

and an oil-soluble coupling component of the formula

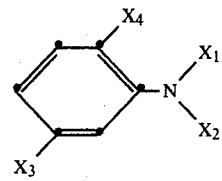

in which $Ar_1$ is aryl or an aromatic heterocyclic radical, $R_1$ is hydrogen, alkyl, aryl, hydroxyl, —(CH$_2$CH$_2$O)$_r$—L$_1$ or —OL$_1$, in which L$_1$ is alkyl and r is 1, 2 or 3, or $R_1$ is

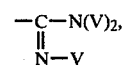

in which V is hydrogen or alkyl, and $R_2$ is alkyl, aryl or —(CH$_2$CH$_2$O)$_r$—L$_1$, or $R_1$ and $R_2$, conjointly with the nitrogen atom to which they are bonded, form a ring, $A_1$ and $A_2$ independently of one another are an amine of the formula —NT$_1$T$_2$, in which T$_1$ and T$_2$ independently of one another are hydrogen, alkyl or aryl, and $X_1$ and $X_2$ independently of one another are hydrogen or alkyl, $X_3$ is hydrogen, alkyl, alkoxy, —O(C$_2$H$_4$O)$_n$-, —H, —O(CH)$_2$)$_m$—OH, —O(CH$_2$)$_m$—OZ$_1$ or —O(CH$_2$CH$_2$O)$_n$—Z$_1$, in which Z$_1$ is alkyl, n is 1 to 5 and m is 2 to 4, or X$_3$ is aryloxy, hydroxyl, halogen, —NHCOY$_1$, —NHCOH, —NHCOOY$_1$, —NHP(O)-(OY$_1$)$_2$ or —NHSO$_2$Y$_1$, in which Y$_1$ is alkyl, —O(CH$_2$-)$_m$—OH, —O(CH$_2$CH$_2$O)$_n$—H, —O(CH$_2$)$_m$—OZ$_1$ or —O(CH$_2$CH$_2$O)$_n$—Z$_1$, or is aryl, and X$_4$ is hydrogen, alkyl, —O(CH$_2$)$_m$—OH, —O(CH$_2$CH$_2$O)$_n$—H, —O(CH$_2$)$_m$—OZ$_1$ or —O(CH$_2$CH$_2$O)$_n$Z$_1$, alkoxy, aryloxy or halogen, and the total of the carbon atoms in the substituents $X_1$, $X_2$, $X_3$ and $X_4$ is at least 10.

The material which has an enhanced sensitivity is treated, after developing the image silver, with an acid processing solution which contains a phase transfer catalyst capable of transferring cations.

The material used in this process exhibits a clearly increased sensitivity.

25 Claims, No Drawings

PROCESS FOR THE PRODUCTION OF PHOTOGRAPHIC COLOR IMAGES BY THE SILVER DYE BLEACH PROCESS

The present invention relates to a process for the production of photographic colour images by the silver dye bleach process, by exposure, silver development, dye formation, dye bleaching, silver bleaching and fixing of a photographic material which, on a transparent or opaque base, contains at least one layer with a light-sensitive silver halide emulsion, it being possible for the dye formation to be carried out simultaneously with the dye bleaching, silver bleaching and fixing or it being possible for the silver bleaching to be carried out simultaneously with the dye bleaching and/or fixing in a single processing bath.

Photographic materials for the production of images by the silver dye bleach process normally contain at least three layers each with a bleachable azo dye, each of which is combined with one light-sensitive silver halide emulsion. To enable the complete range of naturally occurring colours to be reproduced, it has proved advantageous to use one cyan image dye, one magenta image dye and one yellow image dye. The dyes can be either water-soluble azo dyes, the molecular size of which is selected such that they are resistant to diffusion when incorporated in the layers, or they can be oil-soluble dyes which are incorporated as a finely divided dispersion into the layers by conventional methods.

An inherent feature of all silver dye bleach materials is their characteristic of absorbing a substantial proportion of the incident radiation on exposure, due to the incorporated dyes. Of course, this adversely affects the photographic sensitivity. Silver dye bleach materials are therefore really suitable only for printing materials and, in general, are unsuitable as camera films.

One method, by means of which the disadvantages of silver dye bleach materials with incorporated azo dyes can be avoided, comprises, for example, the use of colourless precursors, namely, diazotisable amines and coupling components, in place of the azo dyes themselves. Only after exposure are these components converted into the corresponding azo dyes, by diazotisation of the amines and coupling, and are finally subjected to the silver dye bleach process, with the involvement of the image silver formed by development. Alternatively, either the diazotisable amines or the coupling component can be incorporated in the layers. Formation of the dye is then effected by an after-treatment in a bath which contains the second component. It is also possible, however, for both components to be present in the layer from the start, the after-treatment taking place in a sequence of baths, which effects the diazotisation and coupling under suitable pH conditions and finally ends with the actual silver dye bleach. In every case, it is a prerequisite that the components incorporated in the layers are resistant to diffusion and that neither the incorporated components nor the dye-producing baths interfere with the photographic process.

Silver dye bleach processes, in which the azo image dyes are formed by diazotisation and coupling in the layer, after the exposure and optionally the development of the image silver have taken place, have been proposed in the past in a whole series of patent specifications, for example in British Patent Specification No. 488,853, or in U.S. Pat. Nos. 2,071,688, 2,166,049, 2,333,126, 2,361,541, 2,368,463, 2,514,233 and 2,514,234.

A direct use of diazo compounds which are capable of coupling in photographic layers is in general not possible, because of the low stability of these compounds. For this reason, the diazonium salt is always formed only during the processing of the photographic material, by diazotisation of the corresponding amine, either in a photographic layer or in a previously prepared processing solution. It is known, however, that certain diazonium compounds, such as say diazo-sulfonates or diazoamino compounds and diazonimino compounds (triazenes) are very stable, in contrast to the diazonium salts formed by the reaction with nitrous acid in a solution containing mineral acid, and in some cases are suitable for incorporation in photographic layers.

The use of such stable diazo compounds has been mentioned, for example, in U.S. Pat. Nos. 2,368,463, 2,340,051 and 3,338,711. In particular, the use of triazenes is described in U.S. Pat. Nos. 2,071,688, 2,616,806, 2,653,874 and 2,681,856. Admittedly, stable diazonium compounds of this type have the requisite durability in the photographic layers; since, however, they are not capable of coupling as such, they must first be split into the diazonium salts, which are capable of coupling, in the course of processing by the action of a strong acid. In general, a renewed increase in the pH value is then necessary for coupling. Further processing is then carried out either by the silver dye bleach process or by decomposing the diazonium compound, capable of coupling, on the image silver present.

Admittedly, the use of triazenes and other stable diazonium compounds has the advantage that there is no actual diazotisation reaction during processing. Since, however, the stabilised diazonium compound must first be converted into the diazonium salt which is capable of coupling, an additional processing step is nevertheless necessary.

Furthermore, all the compounds which are to be incorporated in the layers must be resistant to diffusion. In the case of the triazenes, this requirement is not easily met. In most cases, this requires the use of special precipitants and/or mordants, which fix the compound in an insoluble form in the layer. In general, it will be preferable not to incorporate such readily soluble compounds in the layer, but to cause them to diffuse into the layer from a bath in the course of processing. However, this raises a new difficulty, since the diazonium salts being formed from the triazene are readily decomposed by the image silver present. The diffusion of the diazonium compounds into a layer therefore involves the risk of silver images in non-associated layers also being attacked, and this can lead to unintended and very troublesome interaction effects between layers.

In U.S. Pat. No. 2,653,874, a process has been described wherein, to circumvent this difficulty, the image silver present is converted, before splitting of the triazene, into inactive silver halide by oxidation and is redeveloped to metallic silver only after the dye coupling has ended, so that in the end the imagewise dye bleach can take place. This process leads to a very complicated 9-stage processing medhod.

It is thus an object of the present invention to provide a new process for the production of photographic colour images by the silver dye bleach process, using a material of increased sensivity, in which process, after exposure and development, simplified processing to give the colour image is possible.

A process has now been found for the production of photographic colour images by the silver dye bleach process, in which a photographic silver dye bleach material is used that contains at least one layer with finely divided oil droplets, containing a triazene component and a coupling component, and which material after exposure and development with an acid processing solution containing a phase transfer catalyst, gives high-quality photographic colour images.

When a material of this type, after exposure and development of the silver image, is treated with a conventional silver dye bleach bath, with the addition of a phase transfer catalyst, it is possible to effect the three stages, namely 1. splitting of the triazene to give the diazonium salt
2. coupling to give the dye and
3. silver dye bleaching in one working step and thus to obtain a finished colour image which then only requires conventional fixing in order to remove the remaining silver halide.

The present invention therefore relates to a process for the production of photographic colour images by the silver dye bleach process, by exposure, silver development, dye formation, dye bleaching silver bleaching and fixing of a photographic material which, on a transparent or opaque base, contains at least one layer with a light-sensitive silver halide emulsion, it being possible, for the dye formation to be carried out simultaneously with the dye bleaching, silver bleaching and fixing or, it being possible for the silver bleaching to be carried out simultaneously with the dye bleaching and/or fixing in a single processing bath, wherein the light-sensitive silver halide emulsion layer or layers, or a layer or layers adjacent to this or these silver halide emulsion layer or layers in each case, contains or contain, dispersed in oil, an oil-soluble triazene of the formula

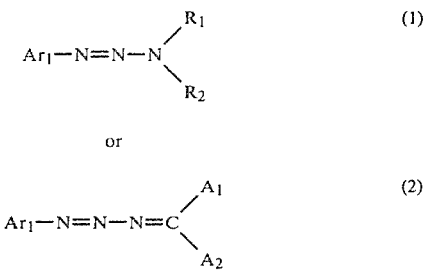

or

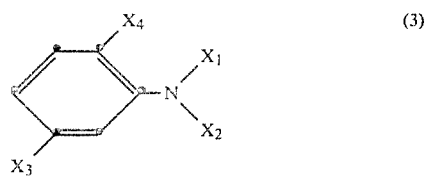

and an an oil-soluble coupling component of the formula

in which $Ar_1$ is substituted or unsubstituted aryl or a substituted or unsubstituted aromatic heterocyclic radical, $R_1$ is hydrogen, substituted or unsubstituted alkyl having 1 to 6 carbon atoms, $-(CH_2CH_2O)_r-L_1$ or $-OL_1$, in which $L_1$ is alkyl having 1 to 12 carbon atoms and r is 1, 2 or 3, or $R_1$ is substituted or unsubstituted aryl, hydroxyl or a radical of the formula

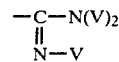

in which V is hydrogen or alkyl having 1 to 12 carbon atoms, $R_2$ is substituted or unsubstituted alkyl having 1 to 6 carbon atoms, $-(CH_2CH_2O)_r-L_1$, with $L_1$ and r being as defined above, or substituted or unsubstituted aryl, or $R_1$ and $R_2$, conjointly with the nitrogen atoms to which they are bonded, form a substituted or unsubstituted, saturated or unsaturated 5-membered, 6-membered or 7-membered ring which may contain a further hetero-atom, $A_1$ and $A_2$ independently of one another are an amino group of the formula $$-N\begin{matrix}T_1\\T_2\end{matrix}$$

in which $T_1$ and $T_2$ independently of one another are hydrogen, substituted or unsubstituted alkyl having 1 to 12 carbon atoms or substituted or unsubstituted aryl, $X_1$ and $X_2$ independently of one another are hydrogen or substituted or unsubstituted alkyl having 1 to 20 carbon atoms, $X_3$ is hydrogen, substituted or unsubstituted alkyl having 1 to 6 carbon atoms, substituted or unsubstituted alkoxy having 1 to 20 carbon atoms, $-O(C_2H_4O)_n-H$, $-O(CH_2)_m-OH$, $-O(CH_2)_m-OZ_1$ or $-O-(C_2H_4O)_n-Z_1$, in which $Z_1$ is alkyl having 1 to 8 carbon atoms, n is an integer from 1 to 5, and m is 2, 3 or 4, or $X_3$ is substituted or unsubstituted aryloxy, hydroxyl, halogen, $-NHCO-Y_1$, NHCOH, $-NHCO-OY_1$, $-NHP(O)(OY_1)_2$ or $-NHSO_2-Y_1$, in which $Y_1$ is substituted or unsubstituted alkyl having 1 to 16 carbon atoms, $-O(C_2H_4O)_n-H$, $-O(CH_2)_m-OH$, $-O(CH_2)_m-OZ_1$ or $-O(C_2H_4O)_n-Z_1$, with $Z_1$, m and n being as defined above, or $Y_1$ is substituted or unsubstituted aryl, and $X_4$ is hydrogen, substituted or unsubstituted alkyl having 1 to 12 carbon atoms, $-O(C_2H_4O)_n-H$, $-O(CH_2)_m-OH$, $-O(CH_2)_m-OZ_1$ or $-O-(C_2H_4O)_n-Z_1$, with $Z_1$, m and n being as defined above, or $X_4$ is substituted or unsubstituted alkoxy having 1 to 16 carbon atoms, substituted or unsubstituted aryloxy or halogen, and the total of the carbon atoms in the substituents $X_1$, $X_2$, $X_3$ and $X_4$ is at least 10; and, after development of the image silver, the material is treated with an acid processing solution which contains a phase transfer catalyst capable of transferring cations.

The invention also relates to a photographic material which is suitable for the process according to the invention.

The invention also relates to formulations for processing the material used in the process according to the invention.

Adjacent layers are to be understood as those layers which, due to their mutual relative positions, favour the exchange of chemical species—molecules or ions. The term therefore comprises also those layers which are not directly adjacent but which optionally are separated from one another by one or more thin layers which do not impede diffusion.

The substituent $Ar_1$ is substituted or unsubstituted aryl. Possible aryl radicals are phenyl and naphthyl, phenyl being preferred. These radicals can be substituted by alkyl or alkoxy each having 1 to 4 carbon atoms, for example n-butyl, i-butyl, t-butyl, n-propyl, i-propyl or preferably ethyl or methyl, or n-butoxy, i-butoxy, t-butoxy, n-propoxy, i-propoxy or preferably ethoxy or methoxy. The alkyl radicals can be substituted further by a halogen, for example fluorine, chlorine or bromine. Examples of preferred radicals are —$CF_3$, —$C_2F_5$, —$CCl_3$ or —$CBr_3$. Further possible substituents are: carboxyl (—COOH) or carbalkoxy, the alkoxy moiety containing 2 to 12, preferably 2 to 7, carbon atoms. A particularly suitable carbalkoxy radical contains 2 to 4 carbon atoms in the alkoxy moiety.

These alkoxy moiety groupings can contain either straight-chain or branched carbon radicals. Further substituents on the aryl radical can be the radicals —$SO_2T_1$, —$SO_2N(T_1)_2$ and —$SO_2NT_1T_2$. In these, $T_1$ and $T_2$ independently of one another are hydrogen, substituted or unsubstituted alkyl having 1 to 12 carbon atoms or substituted or unsubstituted aryl. Possible substituents on the alkyl radicals are methoxy, hydroxyl or cyano. Alkyl radicals having 1 to 6 carbon atoms, in particular methyl and ethyl are preferred. Aryl radicals $T_1$ and $T_2$ are preferably phenyl which can be substituted further by methyl groups. Further substituents on $Ar_1$ are halogens, for example fluorine, chlorine or bromine, in particular chlorine or bromine, and cyano or nitro.

All the substituents of $Ar_1$, listed so far, can occupy the ortho-position on a naphthyl radical or, preferably, the ortho-positions on a phenyl radical.

Further substituents of $Ar_1$, which can occupy the para-position of a naphthyl radical or preferably a phenyl radical, are: alkyl having 1 to 20 carbon atoms, for example methyl, ethyl, n-propyl, i-propyl, n-butyl, i-butyl, t-butyl, amyl, tert-amyl (1,1-dimethylpropyl), 1,1,3,3-tetramethylbutyl, 1-methylethyl-pentyl, hexyl, 1-methylpentyl, neopentyl, 1-, 2- 3-methylhexyl, heptyl, n-octyl, tert-octyl, 2-ethylhexyl, n-nonyl, i-nonyl. tert-nonyl, decyl, tert-decyl, undecyl, dodecyl, tetradecyl, hexadecyl, octadecyl or eicosyl, alkyl chains having 1 to 16 carbon atoms being preferred, and also alkoxy having 1 to 20, in particular 1 to 16, carbon atoms, these radicals being analogous to said alkyl radicals, carbalkoxy having 2 to 21, in particular 2 to 16, carbon atoms, in which case the alkoxy moiety can be substituted by alkoxy having 1 to 6 carbon atoms, and —$SO_2T_3$, —$SO_2N(T_3)_2$ or —$SO_2NT_1T_3$, in which $T_3$ is alkyl having 1 to 20, preferably 1 to 16, carbon atoms, or a radical of the formula —$(CH_2)_p$—$OT_1$, in which $T_1$ is as defined above and p is 2, 3 or 4, and also halogen, for example fluorine, chlorine or bromine, chlorine and bromine being preferred, cyano, nitro, —$CF_3$, —$C_2F_5$, —$CCl_3$ or —$CBr_3$ or a radical of the formula

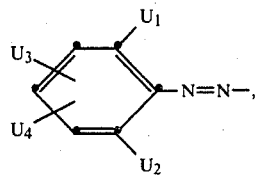

in which $U_1$ and $U_2$ independently of one another are hydrogen, halogen, for example fluorine, chlorine or bromine, preferably chlorine or bromine, cyano, nitro or —$SO_2U_5$, in which $U_5$ is alkyl having 1 to 4 carbon atoms, in particular methyl or ethyl, and $U_3$ is hydrogen, halogen, for which chlorine and bromine are preferred, or nitro. $U_4$ is alkyl or alkoxy each having 1 to 20, in particular 1 to 16, carbon atoms, these radicals corresponding to the abovementioned alkyl and alkoxy groups. Possible substituents on the alkyl and alkoxy groups are halogen, for example fluorine, or alkoxy having 1 to 6 carbon atoms. Trifluoromethyl is a very suitable substituent. $U_4$ can also be —$SO_2T_3$ and —$SO_2NT_1T_3$. $T_1$ and $T_3$ are as defined above. If $U_4$ is carbalkoxy, the alkoxy moiety contains 20, in particular 16, carbon atoms. The alkoxy moiety can be substituted further by alkoxy having 1 to 6 carbon atoms.

The following substituents of $Ar_1$ can occupy the meta-position of a naphthyl ring or, preferably, the meta-positions of a phenyl ring.

Alkyl or alkoxy each having 1 to 20 carbon atoms, examples of these radicals being listed above, and alkyl and alkoxy groups each having 1 to 12 carbon atoms are preferred. Possible substituents of these groups are alkoxy having 1 to 12 carbon atoms, phenoxy or hydroxyl. Another substituent for $Ar_1$ is carbalkoxy having 2 to 21 carbon atoms, in which the alkoxy moiety is unsubstituted or substituted by alkoxy having 1 to 12 carbon atoms, phenoxy or hydroxyl, and —$SO_2T_3$, —$SO_2N(T_3)_2$ and —$SO_2NT_1T_3$, $T_1$ and $T_3$ being as defined above.

A substituent occupying the meta-position of a naphthyl ring or preferably of a phenyl ring can also, together with the substituent in the corresponding para-position, form a radical of the formula —CH=C-$T_4$—CH=CH— or, with the substituent in the corresponding ortho-position, a radical of the formula —$CT_4$=CH—$CT_5$=CH—, in which $T_4$ is hydrogen, nitro, —$SO_2T_3$, —$SO_2N(T_3)_2$ or —$SO_2NT_1T_3$ and $T_5$ is hydrogen, —$OT_3$, —$SO_2T_3$ or —$SO_2NT_1T_3$. $T_1$ and $T_3$ are as defined above.

The total of the carbon atoms in the substituents in the ortho-, meta- and para-positions is at least 8, preferably 10.

$Ar_1$ can also be a substituted or unsubstituted, unsaturated heterocyclic radical. This radical can contain 1 to 3 hetero-atoms, for example oxygen, sulfur and/or nitrogen. 5-membered or 6-membered heterocyclic rings are preferred. They are preferably bonded to the azo grouping via a carbon atom of the rings. Possible substituents of these rings are cyano, nitro, substituted or unsubstituted alkyl having 6 to 18 carbon atoms, substituted or unsubstituted phenyl, or carbalkoxy having 2 to 25 carbon atoms. The following may be mentioned as examples:

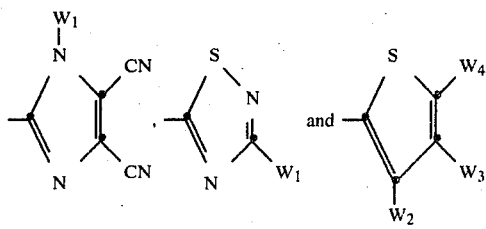

in which $W_1$ is substituted or unsubstituted alkyl having 6 to 18, in particular 6 to 12, carbon atoms, possible substituents being alkoxy having 1 to 4 carbon atoms, and also phenyl which is unsubstituted or substituted by alkyl or alkoxy, each having 6 to 18, in particular 6 to 12, carbon atoms. $W_2$ is carbalkoxy having 2 to 25, in particular 2 to 19, carbon atoms, nitro or cyano. $W_3$ and $W_4$ independently of one another are hydrogen or alkyl having 1 to 6, in particular 1 to 4, carbon atoms. $W_3$ and $W_4$ also can together form a radical of the formulae

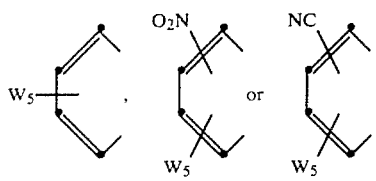

in which $W_5$ is alkyl having 6 to 18, to particular 6 to 12, carbon atoms. Moreover, the total of the carbon atoms in the substituents $W_1$ to $W_5$ is at least 8. The alkyl and alkoxy radicals mentioned for $W_1$ to $W_5$ correspond, with respect to their structure, to the above examples.

$R_1$ is hydrogen or substituted or unsubstituted alkyl having 1 to 6, in particular 1 to 4, carbon atoms. Methyl and ethyl are especially suitable alkyl radicals. Possible substituents of the said alkyl radicals are hydroxyl, methoxy, carboxyl (—COOH), carbalkoxy having 2 to 7, in particular 2, carbon atoms, in which the alkoxy moiety can be substituted by methoxy or cyano, and —$SO_3M$, in which M is hydrogen, ammonium or an alkali metal, preferably sodium or potassium. $R_1$ can also be a radical of the formula —$(CH_2CH_2O)_r$—$L_1$ or —$OL_1$, in which $L_1$ is alkyl having 1 to 12, in particular 1 to 8, carbon atoms. Alkyl having 1 to 6 carbon atoms is particularly suitable. The index r is 1, 2 or 3. If $R_1$ is aryl, phenyl is preferred. The aryl radicals can be substituted by alkyl or alkoxy each having 1 to 6 carbon atoms, for example methyl, ethyl, butyl, hexyl, methoxy, ethoxy, butoxy or hexoxy, or halogen, for example fluorine, chlorine or bromine. $R_1$ can also be hydroxyl or a radical of the formula

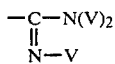

in which V is hydrogen or alkyl having 1 to 12, in particular 1 to 6, carbon atoms.

$R_2$ is substituted or unsubstituted alkyl having 1 to 6 carbon atoms. Methyl and ethyl are preferred. Substituents of these alkyl radicals can be hydroxyl, cyano, methoxy, carboxyl (—COOH), carbalkoxy having 2 to 7, in particular 2, carbon atoms, in which case the alkoxy moiety is unsubstituted or substituted by methoxy or carboxyl (—COOH), or —$SO_3M$, in which M is as defined above. Furthermore, $R_2$ can be —$(CH_2CH_2O)_r$—$L_1$, with $L_1$ and r being as defined above. If $R_2$ is substituted or unsubstituted aryl, phenyl is preferred. These radicals can be substituted by alkyl having 1 to 6 carbon atoms, in particular methyl, or halogen, for example chlorine or bromine. Tolyl, chlorophenyl or bromophenyl are preferred phenyl radicals.

Together with the nitrogen atom to which they are bonded, $R_2$ and $R_1$ can form a 5-membered, 6-membered or 7-membered heterocyclic ring. Nitrogen and oxygen are again possible further hetero-atoms. The heterocyclic radicals can be substituted alkyl having 1 to 6 carbon atoms, in particular methyl. Examples of saturated and unsaturated, bivalent radicals formed from $R_2$ and $R_1$ are: —$(CH_2)_4$—, —$(CH_2)_5$—, —$CH_2CH_2$—O—$CH_2CH_2$—, —$CH_2CH_2$—NH—$CH_2CH_2$—, —$CH_2CH_2$—N($CH_3$)—$CH_2CH_2$—, —CH=N—CH=CH— and —CH=CH—CH=CH—.

Independently of one another, the radicals $A_1$ and $A_2$ are an amino group of the formula —$NT_1T_2$. $T_1$ and $T_2$ are as defined above.

$X_1$ and $X_2$ independently of one another are hydrogen or substituted or unsubstituted alkyl having 1 to 20, in particular 1 to 16, carbon atoms. Examples of possible alkyl radicals are listed above. Suitable substituents are alkoxy having 1 to 4 carbon atoms or carboxyl (—COOH). Particularly preferred alkyl radicals are those of the formula —$CHM_1$—$CH_2M_2$, in which $M_1$ is hydrogen or alkyl having 1 to 4 carbon atoms, in particular methyl or ethyl. $M_2$ is cyano or a radical of the formula —$OM_3$ or —$CO_2M_3$, in which $M_3$ is hydrogen, alkyl having 1 to 16, in particular 1 to 6, carbon atoms, phenyl which is unsubstituted or substituted by alkyl having 1 to 4 carbon atoms, in particular methyl or butyl, or a radical of the formulae —$(C_2H_4O)_n$—$M_4$ or —$(CH_2)_m$—$OM_4$, in which $M_4$ is hydrogen or alkyl having 1 to 4, in particular 1 or 2, carbon atoms. The alkyl radicals can be unsubstituted or substituted by methoxy, cyano or carboxyl (—COOH). The index m is 2, 3 or 4, and n is 1, 2, 3, 4 or 5. $X_1$ is preferably alkyl having 1 to 16 carbon atoms or a radical of the formula —$CHM_1$—$CH_2M_2$, in which $M_1$ and $M_2$ are as defined above, if $X_2$ is hydrogen, alkyl having 1 to 16 carbon atoms, a radical of the formula —$CHM_1$—$CH_2M_2$, benzyl or phenylethyl.

$X_3$ is hydrogen or substituted or unsubstituted alkyl having 1 to 6, in particular 1 to 4, carbon atoms. Suitable substituents of the alkyl radicals are methoxy, carboxyl (—COOH) and cyano. Furthermore, $X_3$ can be alkoxy having 1 to 20, in particular 1 to 16, carbon atoms. Alkoxy radicals having 1 to 6 carbon atoms are very particularly suitable. Examples of such alkoxy radicals are listed above. If $X_3$ is aryloxy, phenoxy which may contain 1 or 2 alkyl substituents having 1 to 4 carbon atoms is preferred. $X_3$ can also be a radical of the formulae —O—$(C_2H_4O)_n$—H, —O—$(CH_2)_m$—OH, —O—$(CH_2)_m$—$OZ_1$ or —O—$(C_2H_4O)_n$—$Z_1$ in which $Z_1$ is alkyl having 1 to 8, preferably 1 to 4, carbon atoms, m is 2, 3 or 4 and n is 1, 2, 3, 4 or 5. Furthermore, $X_3$ can be hydroxyl, halogen, for example fluorine, chlorine or bromine, chlorine and bromine being preferred, or a radical of the formulae —$NHCOY_1$, —$NHCOOY_1$, —NHCOH, —$NHP(O)(OY_1)_2$ or —$NHSO_2Y_1$. $Y_1$ is substituted or unsubstituted alkyl having 1 to 16 carbon atoms. Examples of such alkyl radicals are listed above. Possible substituents of these alkyl radicals are alkoxy having 1 to 4 carbon atoms, carboxyl (—COOH) or cyano. $Y_1$ can also be a radical of the formula —$(C_2H_4O)_n$—H, —$(CH_2)_m$—OH, —$(C_2H_4O)_n$—$Z_1$ or —$(CH_2)_m$—$OZ_1$ in which $Z_1$, n and m are as defined above. $Y_1$ can also be substituted or unsubstituted aryl, in particular phenyl. Suitable substituents of these radicals are 1 or 2 alkyl groups having 1 to 4 carbon atoms.

$X_4$ is hydrogen or substituted or unsubstituted alkyl having 1 to 12 carbon atoms. Examples of such alkyl radicals are listed above. As substituents, they can contain carboxyl (—COOH), hydroxyl, alkoxy and cyano groups, the alkoxy groups having 1 to 6 carbon atoms and preferably being methoxy, ethoxy or butoxy. Preferably, $X_4$ is alkyl having 1 to 8 carbon atoms. These alkyl radicals can be substituted by the substituents indicated. Particularly suitable alkyl radicals $X_4$ contain 1 to 4 carbon atoms. $X_4$ can also be a radical of the formulae —$O(CH_2CH_2O)_n$—H, —$O(CH_2)_m$—OH, —O—$(CH_2CH_2O)_n$—$Z_1$ or —$O(CH_2)_m$—$OZ_1$ in which $Z_1$, m and n are as defined above. Furthermore, $X_4$ can be substituted or unsubstituted alkoxy having 1 to 16, in particular 1 to 8, carbon atoms. Examples of such radicals are listed above. Possible substituents of these are methoxy, ethoxy or carboxyl (—COOH). Alkoxy radicals having 1 to 4 carbon atoms are particularly suitable substituents $X_4$. If $X_4$ is aryloxy, for example naphthoxy or phenoxy, phenoxy is preferred. Possible substituents of the aryl radicals are 1 or 2 alkyl radicals having 1 to 4 carbon atoms. $X_4$ can also be hydroxyl or halogen, for example fluorine, chlorine or bromine, chlorine and bromine being preferred.

The total of the carbon atoms in the substituents $X_1$, $X_2$, $X_3$ and $X_4$ is at least 8. Preferably, the aim is a total of at least 10 carbon atoms.

In a preferred process, the triazene used is of the formula

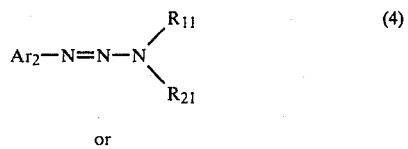

or

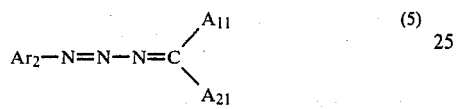

and the oil-soluble coupling component is of the formula

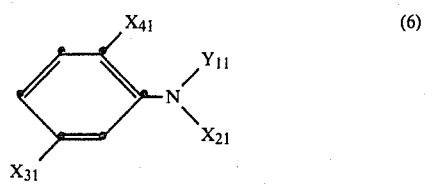

in which $Ar_2$ is a substituted or unsubstituted phenyl, substituted or unsubstituted naphthyl or a substituted or unsubstituted, aromatic radical containing 1 to 3 hetero-atoms, $R_{11}$ is substituted or unsubstituted alkyl having 1 to 6 carbon atoms, —$(CH_2CH_2O)_r$—$L_{11}$ or —$OL_{11}$, in which $L_{11}$ is alkyl having 1 to 8 carbon atoms and r is 1, 2 or 3, or is substituted or unsubstituted phenyl, or hydroxyl, $R_{21}$ is substituted or unsubstituted alkyl having 1 to 6 carbon atoms, —$(CH_2CH_2O)_r$—$L_{11}$, with $L_{11}$ and r being as defined above, or is substituted or unsubstituted phenyl, or $R_{21}$ and $R_{11}$, conjointly with the nitrogen atom to which they are bonded, form a substituted or unsubstituted, saturated or unsaturated 5-membered, 6-membered or 7-membered ring which may contain a further hetero-atom, $A_{11}$ and $A_{21}$ independently of one another are an amino group of the formula

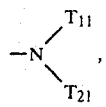

in which $T_{11}$ and $T_{21}$ independently of one another are hydrogen, alkyl having 1 to 12 carbon atoms or phenyl, $X_{11}$ and $X_{21}$ independently of one another are hydrogen or substituted or unsubstituted alkyl having 1 to 16 carbon atoms, $X_{31}$ is hydrogen, substituted or unsubstituted alkyl having 1 to 4 carbon atoms, substituted or unsubstituted alkoxy having 1 to 16 carbon atoms, —$O(C_2H_4O)_n$—H, —$O(CH_2)_m$—OH, —$O(CH_2)_m$—$OZ_{11}$ or —$O$—$(C_2H_4O)_n$—$Z_{11}$, in which $Z_{11}$ is alkyl having 1 to 4 carbon atoms and m and n are as defined above, or $X_{31}$ is substituted or unsubstituted phenoxy, hydroxyl, halogen, —NHCO—$Y_2$, —NHCO—$OY_2$, —NHCOH, —NHP(O)($OY_2)_2$ or —NHSO$_2$—$Y_2$, in which $Y_2$ is substituted or unsubstituted alkyl having 1 to 16 carbon atoms, —$(C_2H_4O)_n$—H, —$(CH_2)_m$—OH, —$(CH_2)_m$—$OZ_{11}$ or —$(C_2H_4O)_n$—$Z_{11}$, with $Z_{11}$, n and m being as defined above, or $Y_2$ is substituted or unsubstituted phenyl, and $X_{41}$ is hydrogen, substituted or unsubstituted alkyl having 1 to 8 carbon atoms, —$O(C_2H_4O)_n$—H, —$O(CH_2)_m$—OH, —$O(CH_2)_m$—$OZ_{11}$ or —$O$—$(C_2H_4O)_n$—$Z_{11}$, with $Z_{11}$, m and n being as defined above, or $X_{41}$ is substituted or unsubstituted alkoxy having 1 to 16 carbon atoms, substituted or unsubstituted phenoxy or halogen, the total of the carbon atoms and the substituents $X_{11}$, $X_{21}$, $X_{31}$ and $X_{41}$ being at least 10.

Preferred triazenes of the formula (4) and coupling components of the formula (6) are those of the formula

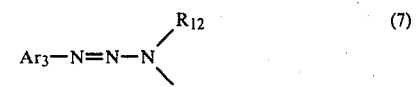

and

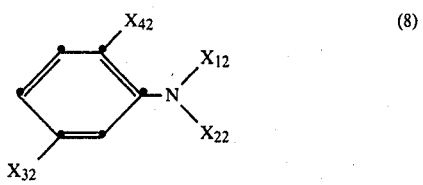

in which $Ar_3$ is substituted or unsubstituted phenyl or substituted or unsubstituted naphthyl, $R_{12}$ is alkyl having 1 to 6 carbon atoms, which is unsubstituted or substituted by hydroxyl, cyano, methoxy, carboxyl, carbalkoxy having 2 to 7 carbon atoms, in which the alkoxy moiety can be further substituted, or by —$SO_3M$, in which M is hydrogen, ammonium or an alkali metal, or $R_{12}$ is —$(CH_2CH_2O)_r$—$L_{11}$ or —$OL_{11}$, with $L_{11}$ and r being as defined above, or phenyl which is unsubstituted or substituted by alkyl or alkoxy each having 1 to 6 carbon atoms or by halogen, or is hydroxyl, $R_{22}$ is alkyl having 1 to 6 carbon atoms, which is unsubstituted or substituted by hydroxyl, cyano, methoxy, carboxyl, carbalkoxy having 2 to 7 carbon atoms, in which the alkoxy moiety can be further substituted, or by —$SO_3M$, in which M is hydrogen, ammonium or an alkali metal, or $R_{22}$ is —$(CH_2CH_2O)_r$—$L_{11}$, with $L_{11}$ and r being as defined above, or phenyl which is unsubstituted or substituted by alkyl having 1 to 6 carbon atoms or halogen, or $R_{22}$ and $R_{12}$, conjointly with the nitrogen atom to which they are bonded, form a saturated or unsaturated 5-membered, 6-membered or 7-membered ring which is unsubstituted or substituted by alkyl having 1 to 6 carbon atoms and may contain a nitrogen atom or oxygen atom as a further heteroatom, $X_{12}$ and $X_{22}$ independently of one another are hydrogen, alkyl having 1 to 16 carbon atoms, benzyl, phenylethyl or a radical of the formula —$CHM_1$—$CH_2M_2$, in which $M_1$ is hydrogen or alkyl having 1 to 4 carbon atoms and $M_2$ is cyano or a radical of the formula —$OM_3$ or —$CO_2M_3$, in which $M_3$ is hydrogen, alkyl having 1 to 16 carbon atoms, phenyl which is unsubstituted or substituted by alkyl having 1 to 4 carbon atoms, or a radical of the formula —$(C_2H_4O)_n$—$M_4$ or —$(CH_2)_m$—$OM_4$, in which $M_4$ is hydrogen or substituted or unsubstituted alkyl having 1 to 4 carbon atoms, and n and m are as defined above, $X_{32}$ is hydrogen, alkyl having 1 to 4 carbon atoms, alkoxy having 1 to 16 carbon atoms, —$O(C_2H_4O)_n$—H, —$O(CH_2)_m$—OH, —$O(C_2H_4O)_m$—$Z_{11}$ or —$O(CH_2)_m$—$OZ_{11}$ with $Z_{11}$ being as defined above and n and m being as defined above, or $X_{32}$ is phenoxy, hydroxyl, halogen, —NHCO—$Y_3$, —NH-COH, —NHCO—$OY_3$, —NHP(O)($OY_3$)$_2$ or —NH-$SO_2$—$Y_3$, in which $Y_3$ is alkyl having 1 to 16 carbon atoms, phenyl which is unsubstituted or substituted by alkyl having 1 to 4 carbon atoms or is a radical of the formula —$(C_2H_4O)_n$—H, —$(CH_2)_m$—OH, —$(C_2H_4O)_m$—$Z_{11}$ or —$(CH_2)_m$—$OZ_{11}$, with $Z_{11}$, n and m being as defined above, and $X_{42}$ is hydrogen, alkyl having 1 to 6 carbon atoms, halogen, alkoxy having 1 to 8 carbon atoms, or —$O(C_2H_4O)_n$—H, —$O(CH_2)_m$—OH, —$O(CH_2)_m$—$OZ_{11}$ or —$O(C_2H_4O)_n$—$Z_{11}$, with $Z_{11}$, n and m being as defined above, or $X_{42}$ is substituted or unsubstituted phenoxy, the total of the carbon atoms in the substituents $X_{12}$, $X_{22}$, $X_{32}$ and $X_{42}$ being at least 10.

Preferred triazenes of the formula (7) are those of the formula

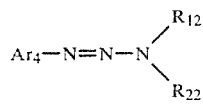 (9)

in which $Ar_4$ is of the formula

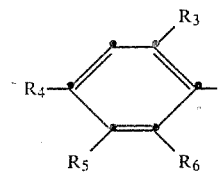

in which $R_3$ and $R_6$ independently of one another are hydrogen, substituted or unsubstituted alkyl or alkoxy each having 1 to 4 carbon atoms, carboxyl, carbalkoxy having 2 to 12 carbon atoms, —$SO_2T_1$, —$SO_2N(T_1)_2$ or —$SO_2NT_1T_2$, in which $T_1$ and $T_2$ are as defined above, halogen, cyano or nitro, $R_4$ is hydrogen, substituted or unsubstituted alkyl or alkoxy each having 1 to 20 carbon atoms, carbalkoxy having 2 to 21 carbon atoms, in which the alkoxy moiety can be further substituted, —$SO_2T_3$, —$SO_2N(T_3)_2$ or —$SO_2NT_1T_3$, in which $T_3$ is alkyl having 1 to 20 carbon atoms or —$(CH_2)_p$—$OT_1$, $T_1$ is as defined above and p is 2, 3 or 4, or $R_4$ is halogen, trifluoromethyl, cyano, nitro or a radical of the formula

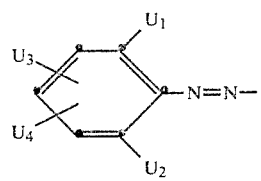

in which $U_1$ and $U_2$ independently of one another are hydrogen, —$SO_2U_5$, in which $U_5$ is alkyl having 1 to 4 carbon atoms, or are halogen, cyano or nitro, $U_3$ is hydrogen, halogen or nitro and $U_4$ is substituted or unsubstituted alkyl or alkoxy each having 1 to 20 carbon atoms, —$SO_2T_3$, —$SO_2NT_1T_3$, in which $T_1$ and $T_3$ are as defined above, or carbalkoxy having 2 to 21 carbon atoms, in which the alkoxy moiety can be further substituted, $R_5$ is hydrogen, substituted or unsubstituted alkyl or alkoxy each having 1 to 20 carbon atoms, carbalkoxy having 2 to 21 carbon atoms, in which the alkoxy moiety can be further substituted, —$SO_2T_3$, —$SO_2N(T_3)_2$ or —$SO_2NT_1T_3$, in which $T_1$ and $T_3$ are as defined above, or $R_5$ conjointly with $R_4$ forms a radical of the formula

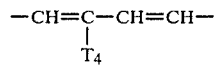

or $R_5$ conjointly with $R_6$ forms a radical of the formula

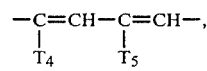

in which $T_4$ is hydrogen, nitro, —$SO_2T_3$, —$SO_2N(T_3)_2$ or —$SO_2NT_1T_3$ and $T_5$ is hydrogen, —$OT_3$, —$SO_2T_3$ or —$SO_2NT_1T_3$, $T_1$ and $T_3$ being defined as above, the total of the carbon atoms in the substituents $R_3$, $R_4$, $R_5$ and $R_6$ being at least 8, and $R_{12}$, $R_{22}$ as well as $X_{12}$, $X_{22}$, $X_{32}$ and $X_{42}$ being as defined above.

The triazenes of the formula (9) are preferably used in combination with the coupling component of the formula (8).

Preferred triazenes of th formula (9) are those of the formula

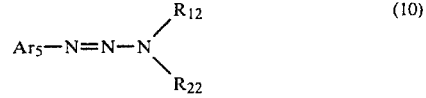 (10)

in which $Ar_5$ is of the formula

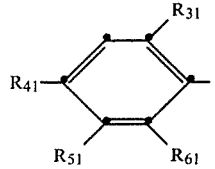

in which $R_{31}$ and $R_{61}$ independently of one another are hydrogen, alkyl or alkoxy each having 1 or 2 carbon atoms, trifluoromethyl, carboxyl, carbalkoxy having 2 to 7 carbon atoms, —$SO_2T_{11}$, —$SO_2N(T_{11})_2$ or —$SO_2NT_{11}T_{21}$, in which $T_{11}$ and $T_{21}$ are as defined above, or are fluorine, chlorine, bromine, cyano or nitro, $R_{41}$ is hydrogen, alkyl having 1 to 20 carbon atoms, trifluoromethyl, alkoxy having 1 to 20 carbon atoms, which is unsubstituted or substituted by alkoxy having 1 to 6 carbon atoms, or is carbalkoxy having 2 to 21 carbon atoms, in which the alkoxy moiety is unsubstituted or substituted further by alkoxy having 1 to 6 carbon atoms, or is —$SO_2T_{31}$, —$SO_2N(T_{31})_2$ or —$SONT_{11}T_{31}$, in which $T_{31}$ is alkyl having 1 to 20 carbon atoms or —(CH$_2$)$_p$—OT$_{11}$, in which T$_{11}$ is as defined above and p is 2, 3 or 4, or R$_4$ is chlorine, bromine, cyano, nitro or a radical of the formula

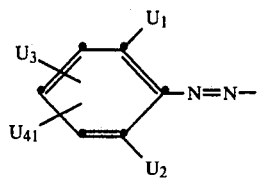

in which U$_{41}$ is hydrogen, alkyl having 1 to 20 carbon atoms, trifluoromethyl, alkoxy having 1 to 20 carbon atoms, which is unsubstituted or substituted by alkoxy having 1 to 6 carbon atoms, or is —SO$_2$T$_{31}$, —SO$_2$NT$_{11}$T$_{31}$, in which T$_{11}$ and T$_{31}$ are as defined above, or is carbalkoxy having 2 to 21 carbon atoms in which the alkoxy moiety is unsubstituted or further substituted by alkoxy having 1 to 6 carbon atoms, R$_{51}$ is hydrogen, alkyl having 1 to 20 carbon atoms, alkoxy having 1 to 20 carbon atoms, which is unsubstituted or substituted by alkoxy having 1 to 12 carbon atoms or by hydroxyl, or is carbalkoxy having 2 to 21 carbon atoms, in which the alkoxy moiety is unsubstituted or substituted by alkoxy having 1 to 12 carbon atoms, or is —SO$_2$T$_{31}$, —SO$_2$N(T$_{31}$)$_2$ or —SO$_2$NT$_{11}$T$_{31}$, in which T$_{11}$ and T$_{31}$ are as defined above, or R$_{51}$ conjointly with R$_{41}$ forms a radical of the formula

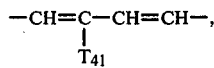

or R$_{51}$ conjointly with R$_{61}$ forms a radical of the formula

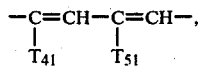

in which T$_{41}$ is hydrogen, nitro, —SO$_2$T$_{31}$, —SO$_2$N(T$_{31}$)$_2$ or —SO$_2$NT$_{11}$T$_{31}$ and T$_{51}$ is hydrogen, —OT$_{31}$, —SO$_2$T$_{31}$ or —SO$_2$NT$_{11}$T$_{31}$, in which T$_{11}$ and T$_{31}$ are as defined above, the total of the carbon atoms in the substituents R$_{31}$, R$_{41}$, R$_{51}$ and R$_{61}$ being at least 10, and R$_{12}$, R$_{22}$ as well as U$_1$, U$_2$ and U$_3$ being as defined above.

Preferably, the triazenes of the formula (10) are used in combination with the coupling components of the formula (8). Preferred coupling components of the formula (8) are those of the formula

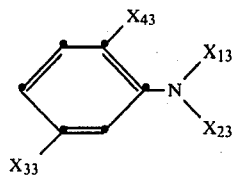

(11)

in which X$_{13}$ is alkyl having 1 to 16 carbon atoms or a radical of the formula —CHM$_1$—CH$_2$M$_2$, in which M$_1$ and M$_2$ are as defined above, X$_{23}$ is hydrogen, alkyl having 1 to 16 carbon atoms, a radical of the formula —CHM$_1$—CH$_2$M$_2$, in which M$_1$ and M$_2$ are as defined above, or is benzyl or phenylethyl, X$_{33}$ is hydrogen, alkyl having 1 to 4 carbon atoms, alkoxy having 1 to 12 carbon atoms, —O(C$_2$H$_4$O)$_n$—Z$_{11}$ or —O(CH$_2$)$_m$—OZ$_{11}$, in which Z$_{11}$, n and m are as defined above, or is phenoxy, hydroxyl, chlorine, bromine, —NH-CO—Y$_3$, —NHCOH, —NHCO—OY$_3$, —NHP(O)-(OY$_3$)$_2$ or —NHSO$_2$—Y$_3$, in which Y$_3$ is as defined above, and X$_{43}$ is hydrogen, alkyl having 1 to 4 carbon atoms, chlorine, bromine, alkoxy having 1 to 8 carbon atoms or —O—(CH$_2$CH$_2$O)$_n$—Z$_{11}$, in which Z$_{11}$ and n are as defined above, the total of the carbon atoms in the substituents X$_{13}$, X$_{23}$, X$_{33}$ and X$_{43}$ being at least 10.

Preferably, the coupling components of the formula (11) are used in combination with the triazenes of the formula (10).

Preferred triazenes of the formula (10) and coupling components (11) are those of the formula

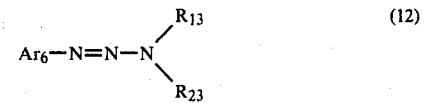

and

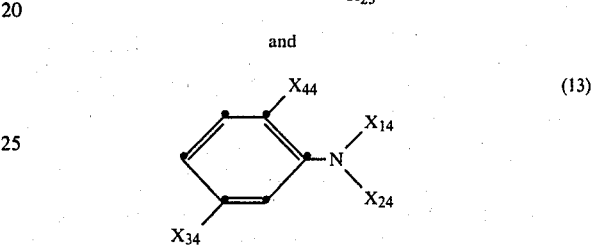

in which Ar$_6$ is of the formula

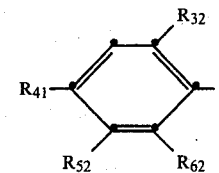

in which R$_{32}$ and R$_{62}$ independently of one another are hydrogen, methyl, methoxy, trifluoromethyl, carbalkoxy having 2 to 4 carbon atoms, —SO$_2$T$_{13}$, —SO$_2$N(T$_{13}$)$_2$ or —SO$_2$NT$_{13}$T$_{23}$, in which T$_{13}$ and T$_{23}$ independently of one another are hydrogen or alkyl having 1 or 2 carbon atoms, or R$_{32}$ and R$_{62}$ are fluorine, chlorine, bromine, cyano or nitro, R$_{52}$ is hydrogen, alkyl having 1 to 20 carbon atoms, —OT$_{31}$, —CO—OT$_{31}$ or —SO$_2$T$_{31}$, in which T$_{31}$ is as defined above, or R$_{52}$ conjointly with R$_{41}$ forms a radical of the formula

or R$_{52}$ conjointly with R$_{62}$ forms a radical of the formula

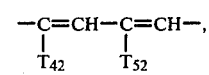

in which T$_{42}$ is hydrogen, nitro, —SO$_2$T$_{32}$ or —SO$_2$N(T$_{32}$)$_2$ and T$_{52}$ is hydrogen, —OT$_{32}$, —SO$_2$T$_{32}$ or —SO$_2$NT$_{12}$T$_{32}$, in which T$_{32}$ is alkyl having 1 to 10 carbon atoms or —(CH$_2$)$_p$—OT$_{12}$ and p and T$_{12}$ as well as R$_{41}$ are as defined above, the total of the carbon atoms in the substituents $R_{32}$, $R_{41}$, $R_{52}$ and $R_{62}$ being at least 10, $R_{13}$ is alkyl having 1 to 4 carbon atoms, alkyl having 1 or 2 carbon atoms, which is unsubstituted or substituted by hydroxyl, cyano, carboxyl, —COOCH$_3$ or methoxy, or is —(CH$_2$CH$_2$O)$_r$—L$_{12}$ or —OL$_{12}$, in which L$_{12}$ is alkyl having 1 to 6 carbon atoms and r is as defined above, or $R_{13}$ is phenyl, tolyl, chlorophenyl, bromophenyl or methoxyphenyl, $R_{23}$ is alkyl having 1 to 4 carbon atoms, alkyl having 1 or 2 carbon atoms, which is unsubstituted or substituted by hydroxyl, cyano, carboxyl, —COOCH$_3$ or methoxy, or is —(CH$_2$CH$_2$O)$_r$—L$_{12}$, in which L$_{12}$ and r are as defined above, or $R_{23}$ is phenyl, tolyl, chlorophenyl or bromophenyl, or $R_{23}$ and $R_{13}$ form a radical of the formula —(CH$_2$)$_4$—, —(CH$_2$)$_5$—, —C$_2$H$_4$—O—C$_2$H$_4$—, —C$_2$H$_4$—NH—C$_2$H$_4$—, —C$_2$H$_4$—N(CH$_3$)—C$_2$H$_4$—, —CH=N—CH=CH— or —CH=CH—CH=CH—, and X$_{14}$ is alkyl having 1 to 16 carbon atoms or a radical of the formula —CHM$_{11}$—CH$_2$M$_{21}$, in which M$_{11}$ is hydrogen, methyl or ethyl and M$_{21}$ is cyano or —OM$_{31}$, in which M$_{31}$ is hydrogen, alkyl having 1 to 6 carbon atoms or phenyl which is unsubstituted or substituted by alkyl having 1 to 4 carbon atoms, X$_{24}$ is hydrogen, alkyl having 1 to 16 carbon atoms or benzyl, X$_{34}$ is hydrogen, alkyl having 1 to 4 carbon atoms, phenoxy, chlorine, hydroxyl, alkoxy having 1 to 6 carbon atoms, —O—CH$_2$CH$_2$—OH, —O—CH$_2$CH$_2$—OZ$_{11}$, —NHCO—Y$_4$, —NHCOH, —NHCO—CH$_2$CH$_2$—OH, —NHCO—CH$_2$CH$_2$—OZ$_{11}$, —NHP(O)(OY$_4$)$_2$, —NHP(O)(OC$_6$H$_4$Y$_5$)$_2$ or —NHSO$_2$Y$_4$, in which Y$_4$ is alkyl having 1 to 16 carbon atoms, Y$_5$ is hydrogen or alkyl having 1 to 6 carbon atoms and Z$_{11}$ is as defined above, and X$_{44}$ is hydrogen, alkyl or alkoxy each having 1 to 4 carbon atoms or —O—(CH$_2$CH$_2$O)$_n$—Z$_{11}$, in which Z$_{11}$ and n are as defined above, the total of the carbon atoms in the substituents X$_{14}$, X$_{24}$, X$_{34}$ and X$_{44}$ being at least 10.

Preferred triazenes of the formula (12) are those of the formula

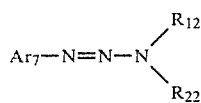
(14)

in which Ar$_7$ is a substituted or unsubstituted, aromatic 5-membered or 6-membered radical which contains 1 to 3 oxygen, sulfur and/or nitrogen atoms and R$_{12}$ and R$_{22}$ are as defined above.

Preferably, the triazenes of the formula (14) are used in combination with the coupling components of the formula (8).

Preferred triazenes of the formula (14) are those of the formula

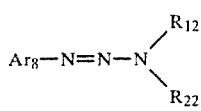
(15)

in which Ar$_8$ is a radical of the formula

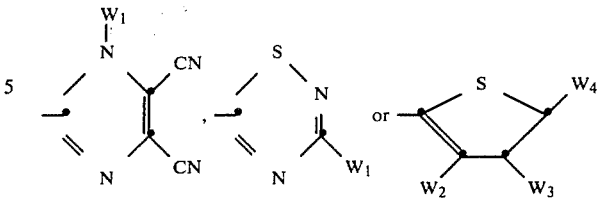

in which W$_1$ is substituted or unsubstituted alkyl having 6 to 18 carbon atoms or substituted or unsubstituted phenyl, W$_2$ is carbalkoxy having 2 to 25 carbon atoms, nitro or cyano, and W$_3$ and W$_4$ independently of one another are hydrogen or alkyl having 1 to 6 carbon atoms, or W$_3$ conjointly with W$_4$ forms a radical of the formula

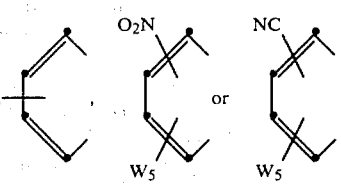

in which W$_5$ is alkyl having 6 to 18 carbon atoms, the total of the carbon atoms in the substituents W$_1$, W$_2$, W$_3$ and W$_4$ being at least 8, and R$_{12}$ and R$_{22}$ being as defined above.

Preferably, the triazenes of the formula (14) are used in combination with the coupling component of the formula (8).

A preferred combination is formed by the triazenes of the formula (15) and the coupling components of the formula (11).

Preferred triazenes of the formula (15) are those of the formula

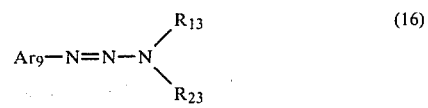
(16)

in which Ar$_9$ is a radical of the formula

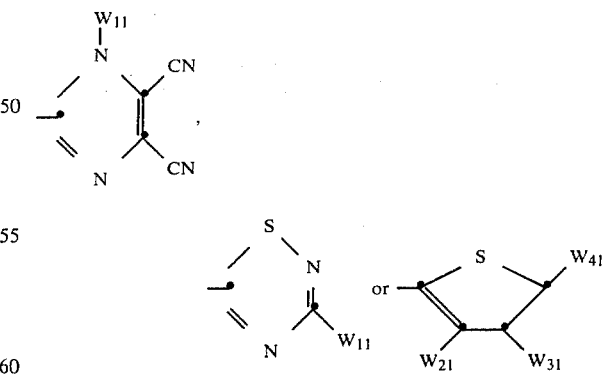

in which W$_{11}$ is alkyl having 6 to 18 carbon atoms or phenyl which is unsubstituted or substituted by alkyl or alkoxy each having 6 to 18 carbon atoms, W$_{21}$ is carbalkoxy having 2 to 19 carbon atoms, nitro or cyano, and W$_{31}$ and W$_{41}$ independently of one another are hydrogen or alkyl having 1 to 4 carbon atoms, or W$_{31}$ and W$_{41}$ conjointly form a radical of the formula

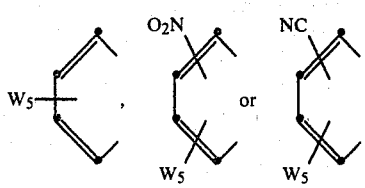

in which $W_5$ is as defined above, the total of the carbon atoms in the substituents $W_{11}$, $W_{21}$, $W_{31}$, $W_{41}$ and $W_5$ being at least 10, and $R_{13}$ and $R_{23}$ being as defined above.

Preferably, the triazenes of the formula (16) are used in combination with the coupling components of the formula (13).

Of great importance is a process, wherein a material is used which, in at least one silver halide emulsion layer, or in one adjacent layer in each case, contains an oil-soluble triazene of the formula (1) or (2) and an oil-soluble coupling component of the formula (3), the triazene and the coupling component having been incorporated, in solution in a water-immiscible solvent or solvent mixture, in a finely divided form into the light-sensitive silver halide emulsion layer or layers or into a layer adjacent to the latter, and, after exposure and development of the image silver, the material is treated with an aqueous processing bath which, for dye formation, contains (a) a strong acid and (b) a cation phase transfer catalyst and optionally for a simultaneously dye bleaching (c) a ligand which forms silver complexes, (d) a dye bleaching catalyst and (e) an anti-oxidising agent and optionally for a simultaneously silver bleaching (f) an oxidising agent and optionally for simultaneously fixing (g) a solvent for silver halide.

In a variant of the process, the aqueous processing bath contains the 7 components (a) to (g).

In a further variant, the aqueous processing bath contains the 6 components (a) to (f), and fixing is carried out in a separate processing bath.

It is also possible for the aqueous processing bath to contain only the 5 components (a) to (e). The silver bleaching and fixing are carried out separately in one or two distinct processing baths.

If the aqueous processing bath contains the two components (a) and (b), the dye bleaching, silver bleaching and fixing are carried out separately in one, two or three distinct processing baths.

The strong acids (component (a)) used can be alkyl sulfonic acids or aryl sulfonic acids and especially p-toluenesulfonic acid, sulfuric acid, sulfamic acid, trichloroacetic acid, or optionally also mixtures of these acids.

The phase transfer catalyst can, for example, be a cation transfer catalyst (component (b)), such as a strong inorganic acid, a perhalogenated aliphatic acid, a benzenesulfonic acid which is substituted by 1 or 2 alkyl or alkoxy groups each having 1 to 12 carbon atoms, a benzenesulfonic acid substituted by 1 to 3 halogen atoms, an alkylsulfonic acid which may be halogenated, having 1 to 12 carbon atoms, a monoalkyl-sulfuric acid having 1 to 12 carbon atoms, or an alkali metal salt or ammonium salt of these acids.

An especially suitable cation transfer catalyst is a hydrogen halide acid, a perhalogenated alkanoic acid having 1 to 6 carbon atoms, a benzenesulfonic acid which is substituted by 1 or 2 alkyl or alkoxy groups each having 1 to 8 carbon atoms, a benzenesulfonic acid which is substituted by 1 to 3 halogen atoms, an alkylsulfonic acid which may be halogenated, having 1 to 8 carbon atoms, a monoalkyl-sulfuric acid having 1 to 8 carbon atoms, or an alkali metal salt or ammonium salt of these acids.

A valuable cation tranfer catalyst is perchloric acid or periodic acid, hydrobromic or hydriodic acid, trifluoro-, trichloro- or tribromo-acetic acid, pentafluoro- or pentachloro-propionic acid, p-toluenesulfonic acid, p-isopropylbenzenesulfonic acid, 2,4-dimethylbenzenesulfonic acid, p-chlorobenzenesulfonic acid, 2,4-dichlorobenzenesulfonic acid, 3,4-dichlorobenzenesulfonic acid, 3,6-dichlorobenzenesulfonic acid, p-methoxybenzenesulfonic acid, p-butoxybenzenesulfonic acid, methanesulfonic acid, ethanesulfonic acid, hexanesulfonic acid, trifluoromethanesulfonic acid or trichloromethanesulfonic acid or a sodium salt, potassium salt or ammonium salt of these acids.

Trifluoro- or trichloro-acetic acid or perchloric acid are very particularly suitable.

The cation transfer catalyst is employed in quantities of 10 to 200 g, in particular 10 to 100 g, per liter of processing solution.

Examples of ligands which form silver complexes (component (c)) are water-soluble iodides, for example alkali metal iodides, and also thiourea or water-soluble, substituted alkylphosphines and arylphosphines. In some cases, components (c) and (g) can be identical.

Component (d) is a diazine derivative. Quinoxalines, pyrazines, phenazines or cinnolines are preferred.

The anti-oxidising agent, component (e), is preferably a reductone or a water-soluble mercapto compound.

Water-soluble, aromatic mononitro or dinitro compounds, or anthraquinonesulfonic acid derivatives are advantageously used as the oxidising agent, component (f).

The photographic material, used according to the invention contains, on an opaque or transparent base, at least one silver halide emulsion layer and, in the same layer or in an adjacent layer or adjacent layers, a dispersion of the oil-soluble triazene of the formula (1) or (2) and of the oil-soluble coupling component of the formula (3) in a stoichiometric ratio, in a water-immiscible solvent or solvent mixture.

In a preferred embodiment, the photographic material contains, in each case in one layer, one red-sensitive, green-sensitive or blue-sensitive silver halide gelatine emulsion and, in each case in the same layer or an adjacent layer, an associated dispersion, which forms the respective complementary colour cyan, magenta or yellow, of a solution of an oil-soluble triazene of the formula (1) or (2) and a coupling component of the formula (3) in a water-immiscible solvet or solvent mixture.

For processing the photographic material used according to the invention, a formulation can be used which contains (a) a strong acid, (b) a phase transfer catalyst, optionally (c) a ligand which forms silver complexes, (d) a dye bleach catalyst, (e) an anti-oxidising agent, optionally (f) an oxidising agent and, optionally (g) a solvent for silver halide.

The triazene components and coupling components used according to the invention are readily soluble in oils, but insoluble in water. Both components are dissolved in oil and are incorporated in a finely dispersed form into a silver halide emulsion layer or into an adjacent layer. In general, these formulations are prepared in such a way that the triazene and the coupling components are present together in the same oil phase, by dissolving the two components together in the oil and subsequently dispersing them, or by preparing two separate oil solutions, mixing these in a suitable ratio and subsequently dispersing them. It is also possible, however, to use two separate oil phases which each contain one component and which are each dispersed separately in a common aqueous phase. Even in this case, adequate mass transfer between the components, which enables dyes to be formed during processing, takes place under the influence of the phase transfer catalyst. An adjacent layer is to be understood as meaning any desired photographic layer, for example a further silver halide emulsion layer or an interlayer. The molar ratio in which the triazene component and the coupling component are dissolved in oil is 4:1 to 1:4, preferably 1:1. Oil means a solvent or solvent mixture, which is immiscible with water.

Suitable oils for the preparation of the solutions of triazenes and coupling components are the customary solvents of low volatility, preferably esters, such as triphenyl phosphate, tricresyl phosphate, phosphates of isopropyl-substituted phenols, dibutyl phthalate or dioctyl phthalate, to which volatile solvents, such as hydrocarbons, halogenated hydrocarbons, ethers, esters, ketones or higher alcohols, for example hexane, methylene chloride, bromobenzene, dichlorobenzene, chloroform, diisopropyl ether, ethyl acetate, butyl acetate, ethyl propionate and similar conventional solvents can also be added in order to assist the dissolution process; if necessary, these can be removed again by evaporation before or after the emulsification.

Suitable light-sensitive silver halide emulsions for the process according to the invention contain silver chloride, silver bromide or silver iodide, or mixtures of these halides, the content of silver iodide as a rule not exceeding 10 mol %. To prepare the emulsions, gelatine is normally used as the protective colloid; however, other water-soluble protective colloids, such as polyvinyl alcohol or polyvinylpyrrolidone, can also be used. It is also possible to replace a part of the gelatine by dispersions of water-insoluble high-molecular substances. For example, dispersion polymers of $\alpha,\beta$-unsaturated compounds, such as acrylates or methacrylates, vinyl esters and vinyl ethers, vinyl chloride, vinylidene chloride and of other mixtures and copolymers are frequently used.

The light-sensitive emulsions can be present in the same layer as the associated oil emulsions which contain the triazenes and coupling components. However, they can also be arranged in a layer which is adjacent to the layer containing the oil emulsions, the imagewise bleaching of the dyes taking place by means of a neighbouring effect, such as is known from German Offenlegungsschriften Nos. 2,036,918, 2,132,835 and 2,132,836.

Formulations which are suitable for carrying out the sequence of reactions described above are, for example, those which are described in German Offenlegungsschriften Nos. 1,924,723, 2,036,918, 2,258,076 or 2,423,814. In addition to a strong acid, a water-soluble iodide and at least one dye bleach catalyst (in most cases a diazine compound), these dye bleach formulations contain an antioxidising agent for the iodide. Formulations of this type rapidly and reliably bleach azo dyes in the presence or metallic silver and have a long storage life. For the subsequent re-halogenation of excess image silver, however, a separate bath containing an oxidising agent, such as a $Fe^{+++}$ or $Cu^{++}$ salt, must be used. A formulation free from heavy metals, as descirbed in German Offenlegungsschrift 2,530,469, can also be used for the silver bleaching.

A silver dye bleach process in which this stage of silver bleaching is combined with the subsequent fixing stage to give a single treatment bath was described, for example, in German Offenlegungsschrift No. 2,309,526. Accordingly, a solvent for silver halide is added as a further component to the formulation.

Processes have also been described in which the stages of the dye bleaching and the silver bleaching are combined in a single bath, for example in German Offenlegungsschriften Nos. 2,448,433, 2,547,720 or 2,831,814. Moreover, a process has been disclosed in which the three steps of (2) dye bleaching, (3) silver bleaching and (4) fixing are carried out in a single bath, as was proposed, for example, in German Patent Specification No. 735,672.

All these variants of the silver dye bleach process can be used for carrying out the present invention, with the proviso that a phase transfer catalyst, which is capable of transporting cations, in particular protons, through the oil/water phase boundary, is also added to the customary constituents of the bath.

The splitting of the triazene and its coupling to give the azo dye can be separated from the subsequent dye bleaching by treating the material with a strongly acid bath which essentially contains only the phase transfer catalyst. Dye bleaching and silver bleaching are then carried out in the customary manner in one or two subsequent treatment stages. Such a reaction sequence will be selected, for example, if the phase transfer catalyst should react in an undesirable manner with a constituent of the dye bleach bath.

Under the action of an acid processing bath containing the phase transfer catalyst, the following process steps can take place:

1. Formation of a free proton, and diffusion into the oil droplets under the influence of the phase transfer catalyst (PTC):

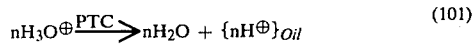
(101)

The subsequent reactions proceed completely within the oil droplets:

2. Splitting of the triazene to give an amine and a free diazonium ion:

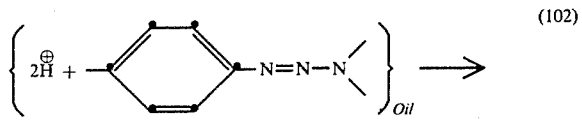
(102)

3. Coupling to give an oil-soluble dye:

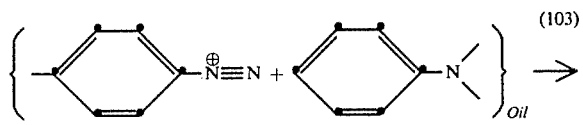
(103)

-continued

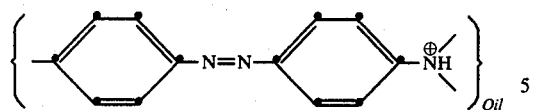

4. L Dye bleach in the presence of metallic silver and of a bleach catalyst (BC):

$4 \text{ Ag}° + 4n\text{Z} +$

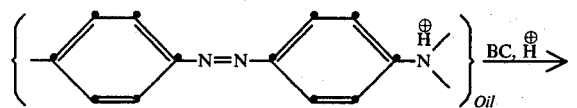

$\xrightarrow{\text{BC, } \overset{\oplus}{\text{H}}}$ (104)

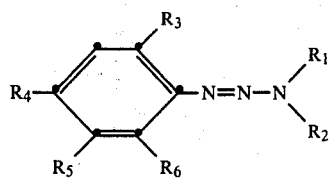

However, it will be understood that the present invention is not restricted on this reaction sequence.

In equation (104), Z is a ligand which can form soluble silver complexes, for example iodide, thiourea, thiosulfate or a substituted water-soluble alkylphosphine or arylphosphine. n is 1, 2, 3 or 4.

Triazenes which are particularly suitable for the process according to the invention are listed in Table 1 which follows.

TABLE 1

Triazines of the formula

(101)

| $R_1$ | $R_2$ | $R_3$ | $R_4$ | $R_5$ | $R_6$ |
|---|---|---|---|---|---|
| $C_2H_5$ | $C_2H_5$ | H | n-$C_{12}H_{25}$ | H | H |
| $CH_3$ | $CH_3$ | H | n-$C_{12}H_{25}$ | H | H |
| $C_2H_4OH$ | —$C_2H_4OH$ | H | n-$C_{16}H_{33}$ | H | H |
| $C_2H_5$ | —$C_2H_5$ | Br | n-$C_{12}H_{25}$ | H | Br |
| —$CH_2CH_2O$—$CH_2CH_2$— | | Br | n-$C_{12}H_{25}$ | H | Br |
| $C_2H_5$ | $C_2H_5$ | Br | n-$C_{12}H_{25}$ | H | H |
| $C_2H_5$ | $C_2H_5$ | H | $CO_2C_8H_{17}$ | H | H |
| $C_2H_5$ | $C_2H_5$ | H | $CO_2C_{10}H_{21}$ | H | H |
| $C_2H_5$ | $C_2H_5$ | H | $CO_2C_{12}H_{23}$ | H | H |
| $C_2H_5$ | $C_2H_5$ | H | $CO_2C_{16}H_{33}$ | H | H |
| $C_2H_5$ | $C_2H_5$ | H | $CO_2C_{18}H_{37}$ | H | H |
| $C_2H_5$ | $C_2H_5$ | $CO_2C_{16}H_{33}$ | H | H | H |
| $CH_3$ | $CH_3$ | H | H | $CO_2C_{16}H_{33}$ | H |
| $CH_2CH_2OH$ | $CH_2CH_2OH$ | H | H | $CO_2C_{16}H_{33}$ | H |
| —$(CH_2)_4$— | | H | H | $CO_2C_{16}H_{33}$ | H |
| —$CH_2CH_2OCH_2CH_2$— | | H | H | $CO_2C_{16}H_{33}$ | H |
| $NCCH_2CH_2$— | $NCCH_2CH_2$— | H | H | $CO_2C_{16}H_{33}$ | H |
| $C_6H_5$ | $CH_3$ | H | H | $CO_2C_{16}H_{33}$ | H |
| $C_6H_5$ | $CH_2CH_2OH$ | H | H | $CO_2C_{16}H_{33}$ | H |
| =$C[N(CH_3)_2]_2$ | | H | H | $CO_2C_{16}H_{33}$ | H |
| $C_2H_5$ | $C_2H_5$ | H | H | $OC_{16}H_{33}$ | H |
| $C_2H_5$ | $C_2H_5$ | H | $SO_2C_{16}H_{33}$ | H | H |
| $CH_2CH_2OH$ | $C_2H_4OH$ | Br | $SO_2C_{16}H_{33}$ | H | Br |
| $C_2H_5$ | $C_2H_5$ | H | H | $CO_2C_{16}H_{33}$ | H |
| $C_2H_4OH$ | $C_2H_4OH$ | H | $SO_2N(C_8H_{17})_2$ | H | H |
| $C_2H_4OH$ | $C_2H_4OH$ | CN | $C_5H_{11}$ | $C_6H_{13}$ | CN |
| p-$CH_3$—$C_6H_4$ | $C_2H_4OH$ | $NO_2$ | $CO_2C_{16}H_{33}$ | H | H |
| $C_2H_4CN$ | $C_2H_4CN$ | H | $NO_2$ | $CO_2C_{12}H_{25}$ | H |
| $C_2H_4OH$ | $C_2H_4OH$ | H | $NO_2$ | $CO_2C_{16}H_{33}$ | H |
| $C_2H_4OH$ | $C_2H_4OH$ | CN | $SO_2N(C_8H_{17})_2$ | H | $NO_2$ |
| $C_2H_4OH$ | $C_2H_4OH$ | CN | $C_{12}H_{25}$ | H | CN |
| $C_2H_4CN$ | $C_2H_4CN$ | $NO_2$ | $NO_2$ | $CO_2C_{12}H_{25}$ | H |
| $C_2H_4OH$ | $C_2H_4OH$ | $NO_2$ | $NO_2$ | $CO_2C_{12}H_{25}$ | CN |
| $C_2H_4OH$ | $C_2H_4OH$ | CN | $SO_2C_{16}H_{33}$ | H | CN |
| $C_2H_4OH$ | $C_2H_4OH$ | $NO_2$ | $NO_2$ | $OC_{16}H_{33}$ | CN |
| $C_2H_5$ | $C_2H_5$ | H | $SO_2N(C_4H_9)_2$ | —CH=CH—CH=CH— | |
| —$CH_2CH_2OCH_2CH_2$— | | H | $SO_2N(C_4H_9)_2$ | —CH=CH—CH=CH— | |
| —$CH_2CH_2OCH_2CH_2$— | | H | $NO_2$ | —CH=CH—C=CH—<br>$\quad\quad\quad$\|<br>$\quad\quad\quad$$OCH_2CH_2CH(CH_3)_2$ | |
| —$CH_2CH_2OCH_2CH_2$— | | H | $NO_2$ | —CH=CH—C=CH—<br>$\quad\quad\quad$\|<br>$\quad\quad\quad$$SO_2N(C_4H_9)_2$ | |

TABLE 1-continued

Triazines of the formula (101)

$$\text{R}_4 \underset{\text{R}_5}{\overset{\text{R}_3}{\bigodot}} \underset{\text{R}_6}{\text{N}=\text{N}-\text{N}} \overset{\text{R}_1}{\underset{\text{R}_2}{}}$$

| $R_1$ | $R_2$ | $R_3$ | $R_4$ | $R_5$ | $R_6$ |
|---|---|---|---|---|---|
| —CH$_2$CH$_2$OCH$_2$CH$_2$— | | CN | NO$_2$ | | —CH=CH—C=CH—<br>$\|$<br>SO$_2$N(C$_4$H$_9$)$_2$ |
| C$_2$H$_4$OH | C$_2$H$_4$OH | NO$_2$ | ⌬—N=N— (with CO$_2$C$_{12}$H$_{25}$) | H | H |
| C$_2$H$_4$OH | C$_2$H$_4$OH | NO$_2$ | H$_{25}$C$_{12}$O$_2$C—⌬—N=N— | H | H |
| C$_2$H$_4$OH | C$_2$H$_4$OH | NO$_2$ | H$_{25}$C$_{12}$O$_2$C—⌬—N=N— | H | CN |
| C$_2$H$_4$OH | C$_2$H$_4$OH | NO$_2$ | (C$_4$H$_9$)$_2$NSO$_2$—⌬—N=N— | H | H |
| C$_2$H$_4$OH | C$_2$H$_4$OH | H | (C$_4$H$_9$)$_2$NSO$_2$—⌬—N=N— | H | H |
| C$_2$H$_4$OH | C$_2$H$_4$OH | NO$_2$ | (C$_4$H$_9$)$_2$NSO$_2$—⌬—N=N— | H | CN |

Coupling components which are particularly suitable for the process according to the invention are indicated in Table 2 which follows.

TABLE 2

Coupling components of the formula (102)

$$X_4 \underset{}{\overset{X_1 \diagdown \diagup X_2}{\underset{\bigodot}{\text{N}}}} X_3$$

| $X_1$ | $X_2$ | $X_3$ | $X_4$ |
|---|---|---|---|
| C$_8$H$_{17}$ | C$_8$H$_{17}$ | H | H |
| C$_2$H$_5$ | C$_2$H$_5$ | OC$_{16}$H$_{33}$ | H |
| C$_8$H$_{17}$ | C$_8$H$_{17}$ | OH | H |
| C$_6$H$_{13}$ | C$_6$H$_{13}$ | OC$_4$H$_9$ | H |
| C$_6$H$_{13}$ | C$_6$H$_{13}$ | OC$_2$H$_4$OCH$_3$ | H |

TABLE 2-continued

Coupling components of the formula

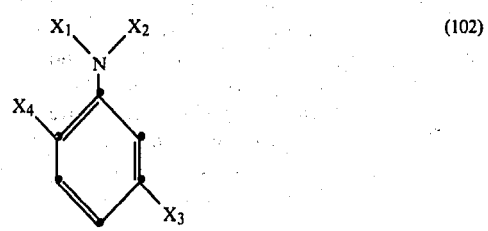

(102)

| $X_1$ | $X_2$ | $X_3$ | $X_4$ |
|---|---|---|---|
| $C_6H_{13}$ | $C_6H_{13}$ | $OCH_3$ | $OCH_3$ |
| $C_8H_{17}$ | $C_8H_{17}$ | $OCH_3$ | $OCH_3$ |
| $C_6H_{13}$ | $C_6H_{13}$ | $OC_2H_4OCH_3$ | $OC_2H_4OCH_3$ |
| $C_{12}H_{23}$ | H | $OCH_3$ | H |
| $C_{12}H_{23}$ | H | $OCH_3$ | $OCH_3$ |
| $C_6H_{13}$ | $C_6H_{13}$ | OH | $OCH_3$ |
| $C_4H_9$ | $C_4H_9$ | $NHCOCH_2CH(CH_3)_2$ | $OCH_3$ |
| $C_6H_{13}$ | $C_6H_{13}$ | $NHCOCH_2CH(CH_3)_2$ | $OCH_3$ |
| $C_6H_{13}$ | $C_6H_{13}$ | $NHCOCH_2CH(CH_3)_2$ | H |
| $C_8H_{17}$ | $C_8H_{17}$ | $NHCOCH_3$ | H |
| $CH_3$ | $CH_3$ | $NHCOC_{11}H_{23}$ | H |
| $C_2H_5$ | $C_2H_5$ | $NHCOC_{11}H_{23}$ | H |
| $C_{12}H_{25}$ | H | $NHCOCH_2CH(CH_3)_2$ | H |
| $C_{10}H_{21}$ | H | $NHCOCH_2CH(CH_3)_2$ | $OCH_3$ |
| $C_2H_4CN$ | H | $NHCOC_{11}H_{23}$ | H |
| $\underset{CH_3}{CHCH_2OCH_3}$ | H | $NHCOC_{11}H_{23}$ | $OCH_3$ |
| $\underset{CH_3}{CH-CH_2CH(CH_3)_2}$ | H | $NHCOC_{11}H_{23}$ | $OCH_3$ |
| $C_6H_{13}$ | $C_6H_{13}$ | $NHCOCH_2CH(CH_3)_2$ | $OC_2H_4OCH_3$ |
| $C_4H_9$ | $C_4H_9$ | $NHCOCH_2CH(CH_3)_2$ | $OCH_2CH_2OCH_3$ |
| $C_2H_4CN$ | H | $NHP(O)(OC_8H_{17})_2$ | H |
| $C_2H_4CN$ | H | $NHP(O)(OC_6H_{13})_2$ | H |
| $C_2H_4CN$ | H | $NHP(O)(OC_6H_5)_2$ | H |
| $C_4H_9$ | $C_4H_9$ | $NHP(O)(OC_2H_5)_2$ | $OCH_3$ |
| $C_6H_{13}$ | $C_6H_{13}$ | $NHP(O)(OC_2H_5)_2$ | H |
| $C_2H_5$ | $C_2H_5$ | $NHP(O)(OC_4H_9)_2$ | $OCH_3$ |
| $C_{12}H_{25}$ | H | $NHCOCH_3$ | H |
| $C_{12}H_{25}$ | H | $NHSO_2CH_3$ | H |
| $C_6H_{13}$ | $C_6H_{13}$ | $NHSO_2CH_3$ | H |
| $C_6H_{13}$ | $C_6H_{13}$ | $NHSO_2CH_3$ | $OCH_3$ |
| $C_2H_4CN$ | H | $NHSO_2C_{12}H_{25}$ | H |
| $CH_2CH_2OH$ | H | $NHCOC_{11}H_{23}$ | H |
| $C_{12}H_{25}$ | H | $NHP(O)(OC_2H_5)_2$ | H |

The triazenes used according to the invention can be prepared by customary methods from the corresponding amines by diazotisation and subsequent condensation of the diazonium salt with an amine.

A further method, starting with nitroso compounds, likewise leads to triazenes by condensation with an asymmetrical hydrazine. The method is especially suitable for heterocyclic triazenes. A detailed description of feasible synthetic methods is to be found, for example, in I. G. Laing, in Rodd's Chemistry of Carbon Compounds, 2nd edition by S. Coffey, volume IIIc, pages 89–102, 1973, Amsterdam, and also in C. Süling, "Methoden zur Herstellung and Umwandlung von aromatischen Triazenen and Höheren Azahomologen" (Methods for the Preparation and Conversion of Aromatic Triazenes and Higher Azahomologs), in Houben-Weyl, Methoden der organischen Chemie (Methods of Organic Chemistry), volume 10/3, pages 699–743 (1965, G. Thieme, Stuttgart), and also in K. H. Saunders, The Aromatic Diazo Compounds and their Technical Applications, 2nd edition, London 1949.

The coupling components used according to the invention are prepared by customary methods, that is to say, for example, by alkylation, acylation, nitration, reduction or cyanoethylation. Coupling components having the grouping

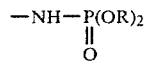

can be prepared by the method given in Swiss Patent Application 3,340/80-0.

EXAMPLE 1

Preparation of the triazene of the formula

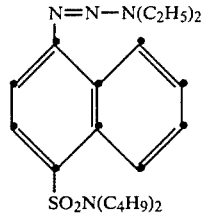

(a) 4-Acetamido-naphthalene-1-sulfochloride is prepared according to German Patent Specification No. 532,399.

(b) 8.5 g (0.03 m) of 4-acetamido-naphthalene-1-sulfochloride are added in portions to a solution of 8.1 g (0.063 m) of dibutylamine in 50 ml of 1,2-dichloroethane. The mixture is stirred for 15 minutes and finally boiled under reflux for 30 minutes. 50 ml of chloroform are added. The mixture is then washed with 2% hydrochloric acid and with water. The organic solution is dried over magnesium sulfate, the solvent is evaporated off and the residue is dried under a high vacuum.

This gives 9.5 g (84%) of 4-acetamido-naphthalene-1-(N,N-dibutyl-sulfonamide).

(c) A mixture of 9.5 g (0.025 m) of 4-acetamido-naphthalene-1-(N,N-dibutyl-sulfonamide), 55 ml of 25% sulfuric acid and 80 ml of ethanol is stirred for 4 hours at 60° C. The mixture is poured into 200 ml of water and neutralised with concentrated ammonia solution. The oily layer is extracted with chloroform. The organic solution is dried over magnesium sulfate and the solvent is evaporated off. The oily residue is dried under a high vacuum.

This gives 8.1 g (96%) of oily 4-amino-naphthalene-1-(N,N-dibutyl-sulfonamide) which crystallises on storage.

(d) 6.7 g (0.02 m) of 4-amino-naphthalene-1-(N,N-dibutyl-sulfonamide) are dissolved in 30 ml of propanol, 12 ml of water and 8 g of concentrated hydrochloric acid. At 5° C., 1.45 g (0.021 m) of sodium nitrite in 10 ml of water are added dropwise. The mixture is stirred for 30 minutes at 5° C. The excess of nitrite is destroyed with sulfamic acid. The diazonium suspension is added in portions to a solution of 8.8 g (0.12 m) of diethylamine in 50 ml of propanol and 50 ml of water. The mixture is stirred for one hour. 100 ml of water are then added. The oily layer is extracted with chloroform, and the extract is washed with water and finally dried over magnesium sulfate. The solvent is evaporated off and the oily residue, on silica gel, is eluted with methylene chloride.

This gives 2.1 g (25%) of 1-[4-(N,N-dibutyl-sulfonamido)-1-naphthyl]-3,3-diethyl-triazene.

The nuclear magnetic resonance spectrum (in CDCl$_3$) and the elemetary analysis confirm the chemical structure of the triazene.

EXAMPLE 2

Preparation of the triazene of the formula

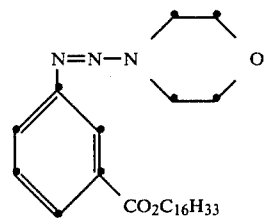

(a) A mixture of 25 g (0.15 m) of 3-nitro-benzoic acid, 40 g (0.165 m) of n-hexadecanol and 3 g of p-toluenesulfonic acid in 300 ml of toluene is boiled under reflux. The water formed is removed by means of a water separator. The solution is cooled, washed with sodium bicarbonate solution and finally dried over magnesium sulfate. The solvent is evaporated off to dryness and the residue is recrystallised from 150 ml of propanol in the presence of animal charcoal. This gives 40 g (68%) of hexadecyl 3-nitro-benzoate (melting point 51°–53° C.).

(b) 39 g (0.099 m) of hexadecyl 3-nitro-benzoate are suspended in 250 ml of 2-methoxy-ethanol, 2 g of 10% palladium-on-carbon catalyst are added and the mixture is subjected to hydrogenation under normal pressure. After the reaction has ended, the catalyst is filtered off under nitrogen. The solvent is evaporated off and the crude product is recrystallised from 150 ml of propanol.

This gives 31 g (87%) of hexadecyl 3-amino-benzoate (melting point 52°–53° C.).

(c) 1.08 g (0.003 m) of hexadecyl 3-amino-benzoate are diazotised in 15 ml of chloroform, in the course of 60 minutes at 5° C. in the presence of 0.6 g (0.006 m) of methanesulfonic acid, with 0.43 g (0.003 m) of 90% nitrosylsulfuric acid. The diazo solution obtained is added dropwise to a solution of 1.75 g (0.020 m) of morpholine in 20 ml of chloroform. The mixture is stirred for one hour. The organic solution is washed three times with water and is dried over magnesium sulfate. The solvent is evaporated off and the residue is recrystallised from 25 ml of acetonitrile.

This gives 1.1 g (80%) of N-(3-hexyldecyloxycarbonyl-phenyl-azo)-morpholine (melting point 40°–42° C.).

The nuclear magnetic resonance spectrum (in CDCl$_3$) and the elementary analysis confirm the chemical structure of the triazene.

Similar compounds can be prepared analogously, for example

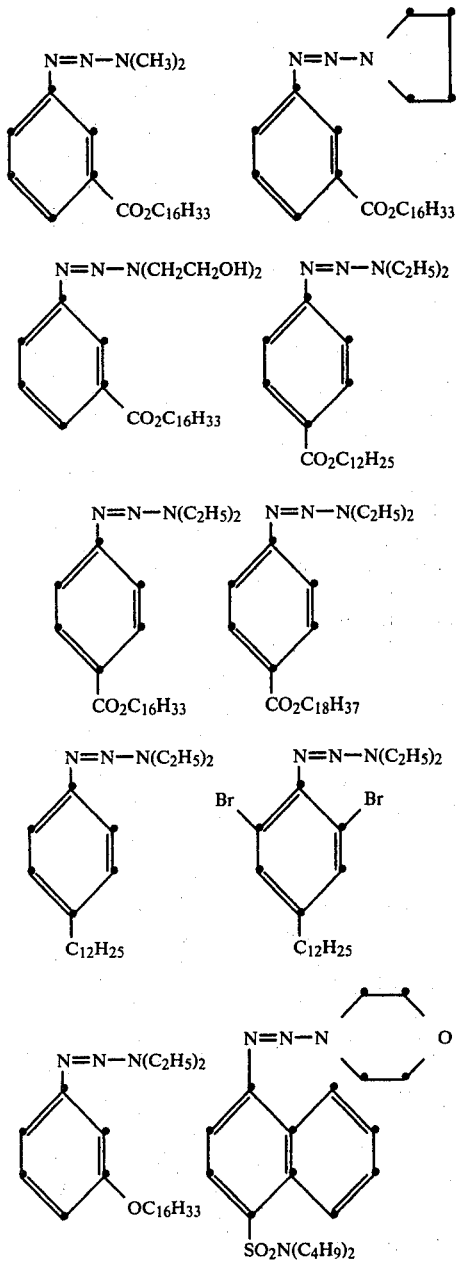

EXAMPLE 3

Preparation of the triazene of the formula

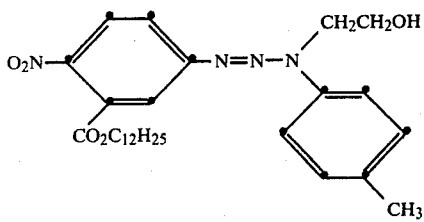

(a) 27.3 g (0.15 m) of 5-amino-2-nitro-benzoic acid are dissolved under nitrogen in 100 ml of N,N-dimethylformamide. 28.4 g (0.158 m) of 30% sodium methylate solution are added. The mixture is stirred for 15 minutes. 100 mg of sodium iodide are added, and finally 39.2 g (0.157 m) of bromododecane are added dropwise. The mixture is heated for four hours at 150° C. (a little methanol distilling off). The reaction mixture is stirred into water. The precipitate is filtered off with suction, washed with water and then with methanol and dried in vacuo. The crude product is recrystallised, in the presence of animal charcoal, from 100 ml of hexane and then from 60 ml of methanol.

This gives 26.8 g (51%) of dodecyl 5-amino-2-nitrobenzoate (melting point 58°-59° C.).

(b) 3.5 g (0.01 m) of dodecyl 5-amino-2-nitro-benzoate are suspended in a mixture of 20 ml of acetic acid and 7.0 g (0.04 m) of a 50% solution of fluoboric acid. 1.3 g (0.011 m) of isopentyl nitrite are added dropwise at room temperature. The mixture is stirred for 30 minutes. The white precipitate is filtered off with suction, washed with water and thoroughly pressed off.

This gives 6 g of moist 3-(dodecyloxycarbonyl)-4-nitro-benzene-diazonium tetrafluoborate.

(c) 3.0 g (about 0.005 m) of moist 3-(dodecyloxycarbonyl)-4-nitro-benzene-diazonium tetrafluoborate are added in portions to a mixture of 0.76 g (0.005 m) of N-(2-hydroxyethyl)-toluidine, 0.6 g (0.0055 m) of sodium carbonate and 30 ml of methanol. The reaction mixture is poured into water, and the precipitate which is forming is filtered off with suction, washed with water and dried in vacuo at 50° C. The crude product is recrystallised from 20 ml of hexane, in the presence of animal charcoal.

This gives 1.25 g (49%) of 1-(3-dodecyloxycarbonyl-4-nitro-phenyl)-3-(2-hydroxyethyl)-3-(p-methyl-phenyl)-triazene (melting point (64°-66° C.).

The nuclear magnetic resonance spectrum (in CDCl₃) and the elementary analysis confirm the chemical structure of the triazene.

EXAMPLE 4

Preparation of the triazene of the formula

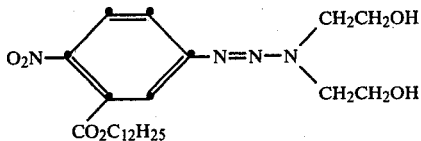

3.0 g (about 0.005 m) of moist 3-(dodecyloxycarbonyl)-4-nitro-benzene-diazonium tetrafluoborate are added in portions to a solution of 2.63 g (0.025 m) of diethanolamine in 30 ml of methanol. The solution is stirred for 30 minutes and finally stirred into water. The oily layer is extracted with chloroform, and the extract is washed with water and finally dried over magnesium sulfonate. The solvent is evaporated off, and the oily residue, on silica gel, is eluted first with a mixture of chloroform (95 parts) and ethyl acetate (5 parts), and finally with a mixture of chloroform (95 parts) and methanol (5 parts).

This gives 2.1 g (90%) of 1-(3-dodecyloxycarbonyl-4-nitro-phenyl)-3,3-bis-(2-hydroxyethyl)-triazene.

The nuclear magnetic resonance spectrum (in CDCl₃) and the elementary analysis confirm the chemical structure of the triazene.

EXAMPLE 5

Preparation of the triazene of the formula

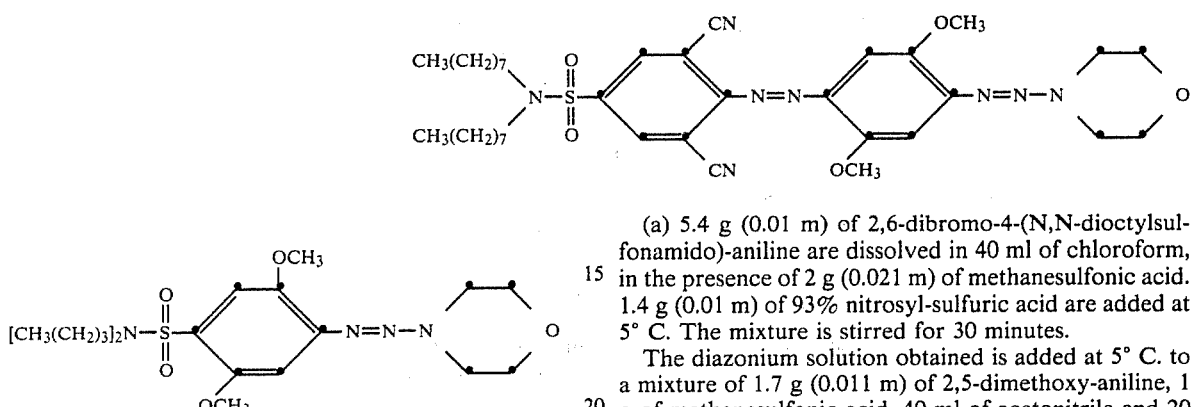

(a) 19.5 g (0.1 m) of 2,5-dimethoxy-acetanilide are added in portions, at 0° C., to 250 ml of chlorosulfonic acid. The mixture is stirred for 30 minutes at 0° C. and then for 3 hours at 40° C. The mixture is then poured into 1,500 ml of ice water. The organic phase is extracted with chloroform. The extract is dried over magnesium sulfate and the solvent is evaporated off. The crude product is recrystallised from a mixture of 200 ml of hexane and 150 ml of ethyl acetate.

This gives 17 g (57.6%) of 2,5-dimethoxy-acetanilide-4-sulfonic acid chloride (melting point 151°–152° C.).

(b) 6.5 g (0.05 m) of dibutylamine are dissolved in 50 ml of methylene chloride, and 5.9 g (0.02 m) of 2,5-dimethoxy-acetanilide-4-sulfonic acid chloride are added in portions. The reaction mixture is boiled for one hour under reflux. After cooling, the solution is washed with dilute aqueous hydrochloric acid and dried over magnesium sulfate. The solvent is evaporated off. The residue is mixed with 60 ml of ethanol and 30 ml of concentrated hydrochloric acid and is heated for 2 hours at 60° C. The mixture is diluted with 200 ml of water and neutralised with sodium hydroxide solution. The oily layer is extracted with methylene chloride and dried over magnesium sulfate. After the solvent has been removed, the oily product is dried in a high vacuum.

This gives 6.6 g (97%) of 2,5-dimethoxy-4-(N,N-dibutylsulfonamido)-aniline (melting point 44°–45° C.).

(c) 3.1 g (0.009 m) of 2,5-dimethoxy-4-(N,N-dibutylsulfonamido)-aniline are dissolved in a mixture of 20 ml of acetic acid and 6.3 g (0.036 m) of 50% aqueous tetrafluoroboric acid. 1.17 g (0.010 m) of isopentyl nitrite are added dropwise at room temperature. The mixture is stirred for 30 minutes. The diazonium solution obtained is added dropwise, at 10° C., to a mixture of 61 g of morpholine, 200 ml of chloroform and 200 ml of water. The reaction mixture is stirred for one hour at 10° C. The organic layer is separated off and washed twice with water. The solvent is evaporated off and the oily crude product, on silica gel, is eluted with a mixture of trichloroethylene (85 parts) and ethyl acetate (15 parts).

This gives 3.9 g (98%) of N-[2,5-dimethoxy-4-(N,N-dibutylsulfonamido)-phenyl-azo]-morpholine in the form of an oil.

The nuclear magnetic resonance spectrum (in CDCl$_3$) and the elementary analysis confirm the chemical structure of the triazene.

EXAMPLE 6

Preparation of the triazene of the formula (a) 5.4 g (0.01 m) of 2,6-dibromo-4-(N,N-dioctylsulfonamido)-aniline are dissolved in 40 ml of chloroform, in the presence of 2 g (0.021 m) of methanesulfonic acid. 1.4 g (0.01 m) of 93% nitrosyl-sulfuric acid are added at 5° C. The mixture is stirred for 30 minutes.

The diazonium solution obtained is added at 5° C. to a mixture of 1.7 g (0.011 m) of 2,5-dimethoxy-aniline, 1 g of methanesulfonic acid, 40 ml of acetonitrile and 20 ml of chloroform. 4.1 g (0.05 m) of sodium acetate are added in portions. The reaction mixture is stirred for one hour at 5° C., then poured into water and extracted with chloroform. The organic phase is washed with water and dried over magnesium sulfate. After removal of the solvent, this gives 7.2 g (100%) of the dye of the formula

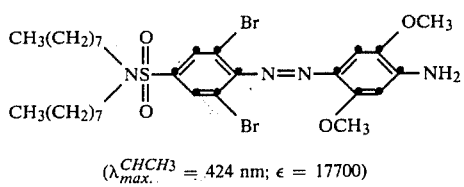

($\lambda_{max.}^{CHCH_3} = 424$ nm; $\epsilon = 17700$)

(b) 7.0 g (0.097 m) of this dye are dissolved in 30 ml of N-methyl-pyrrolidone. 5 g of copper (I) cyanide are added to this solution. The mixture is heated for 30 minutes at 100° C. After cooling, the reaction mixture is stirred for 15 minutes in a solution of sodium thiocyanate. The precipitate is filtered off with suction and washed with water. The crude product is dissolved in 200 ml of chloroform and stirred with magnesium sulfate and silica gel.

The suspension is filtered and the solvent is evaporated off from the filtrate.

This gives 5.4 g (91%) of the dye of the formula

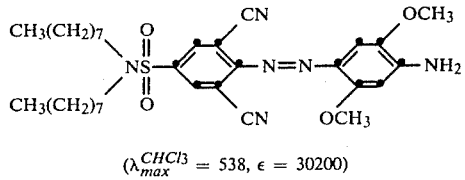

($\lambda_{max}^{CHCl_3} = 538$, $\epsilon = 30200$)

(c) 0.6 g (0.001 m) of this dye is dissolved in 10 ml of methylene chloride, in the presence of 0.2 g (0.002 m) of methanesulfonic acid. 0.25 g (0.002 m) of isopentyl nitrite is added. The mixture is stirred for 90 minutes at room temperature.

The diazonium solution obtained is added dropwise to a mixture of 0.45 g (0.005 m) of morpholine and 10 ml of methylene chloride. The mixture is stirred for one hour and is poured into 50 ml of water. The organic phase is separated off, washed three times with water and dried over magnesium sulfate. The solvent is evaporated off and the residue, on silica gel, is eluted with a mixture of trichloroethylene (8 parts) and ethyl acetate (2 parts).

This gives 350 mg (49.4%) of the triazene of the formula

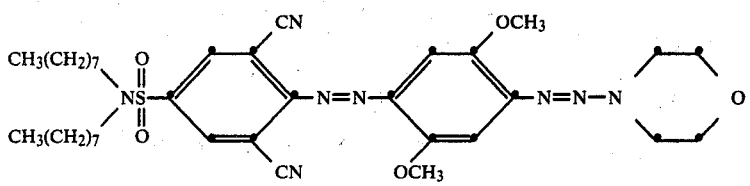

The triazene of the formula

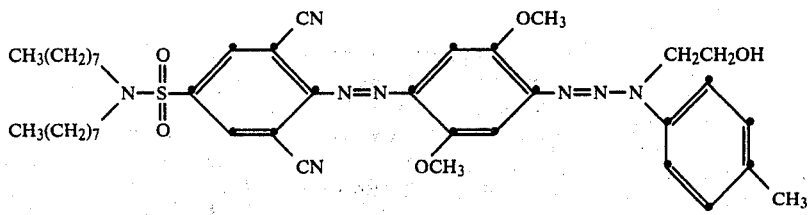

is prepared analogously. (Yield: 32%).

EXAMPLE 7

Preparation of the triazene of the formula

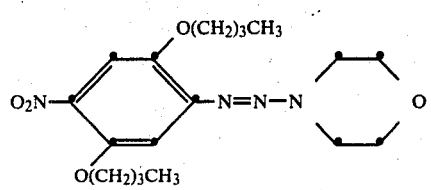

2.82 g (0.01 m) of 2,5-dibutoxy-4-nitro-aniline are suspended in a mixture of 45 ml of acetic acid and 7.0 g (0.04 m) of 50% aqueous tetrafluoroboric acid. 1.4 g (0.012 m) of isopentyl nitrite are added dropwise. The mixture is stirred for one hour. After addition of 10 ml of water, the precipitate which has formed is washed with water and added in portions to a mixture of 6 g of morpholine and 30 ml of methanol. The suspension is stirred for 30 minutes and introduced into 30 ml of water. The precipitate is filtered off with suction. The crude product is recrystallised from 25 ml of methanol.

This gives 3.1 g (81.4%) of N-(2,5-dibutoxy-4-nitro-phenyl-azo)-morpholine (melting point 79°-81° C.).

The nuclear magnetic resonance spectrum (in CDCl$_3$) and the elementary analysis confirm the chemical structure of the triazene.

EXAMPLE 8

Preparation of the coupling component of the formula

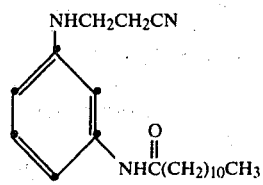

(a) 21.6 g (0.2 mol) of 1,3-phenylenediamine, 10.6 g (0.2 mol) of acrylonitrile, 5 g of acetic acid and 100 ml of water are heated for 6 hours at 100° C. The reaction mixture is neutralised with sodium carbonate and extracted with methylene chloride. The extract is dried over magnesium sulfate. The solvent is evaporated off and the remaining oily residue is distilled under a high vacuum.

This gives 16.2 g (50.2%) of 3-[N-(2-cyanoethyl)-amino]-aniline (boiling point 160°-164° C./0.1 mm Hg).

(b) 0.97 g (0.006 mol) of 3-[N-(2-cyanoethyl)-amino]-aniline is dissolved in 10 ml of dry toluene and 5 ml of dry dioxane. 0.67 g (0.0066 mol) of triethylamine is added to this solution. 1.34 g (0.0061 mol) of lauric acid chloride are added dropwise. The reaction mixture is stirred for 3 hours. The precipitate of triethylamine hydrochloride is filtered off, and the filtrate is evaporated to dryness. The residue is recrystallised twice from a mixture of 10 ml of hexane and 2.5 ml of ethyl acetate.

This gives 0.9 g (44%) of 3-(laurylamido)-N-2-cyano-ethyl)-aniline (melting point 101°-103° C.).

The nuclear magnetic resonance spectrum (in CDCl$_3$) and the elementary analysis confirm the chemical structure of the coupling component.

EXAMPLE 9

Preparation of the coupling component of the formula

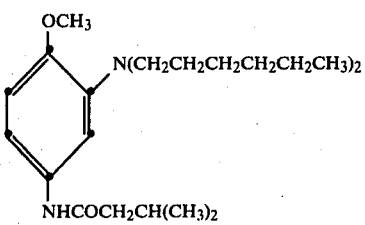

(a) 84 g (0.5 m) of 4-amino-2-nitro-anisole are dissolved in 500 ml of dry dioxane. 65 g (0.65 m) of calcium carbonate are added. 66.3 g (0.55 m) of isovaleric acid chloride are then added dropwise at 15° C. The suspension is stirred for two hours at room temperature and is then filtered with suction; the solid residue is extracted with a further 300 ml of dioxane; the organic solutions are collected and evaporated to dryness. The crude product is recrystallised from 250 ml of toluene, in the presence of animal charcoal.

This gives 86.9 g (69%) of 4-isovalerylamido-2-nitro-anisole (melting point 100°–101° C.).

(b) 86 g (0.34 m) of 4-isovalerylamido-2-nitro-anisole are dissolved in 500 ml of 2-methoxy-ethanol, 2 g of 10% palladium-on-carbon catalyst are added and the mixture is subjected to hydrogenation under normal pressure. After the reaction has ended, the catalyst is filtered off under nitrogen. The solvent is evaporated off and the crude product is recrystallised from 300 ml of toluene, in the presence of animal charcoal.

This gives 48 g (64%) of 2-amino-4-isovalerylamidoanisole (melting point 111°–113° C.).

(c) 13.35 g (0.06 m) of 2-amino-4-isovalerylamidoanisole are dissolved under nitrogen in 200 ml of N,N-dimethylacetamide. 10 g (0.25 m) of magnesium oxide and 33 g (0.2 m) of hexyl bromide are added. The mixture is heated for 6 hours at 130° C. and is then cooled down. The suspension is filtered with suction and the filtrate is poured into 100 ml of ice water. The oily product is extracted with hexane, the organic solution is dried over magnesium sulfate and, finally, the solvent is evaporated off. The oily residue, on silica gel, is eluted with chloroform. This gives 20.9 g (89%) of 2-methoxy-5-isovalerylamido-N,N-dihexyl-aniline (melting point 26°–28° C.).

The nuclear magnetic resonance spectrum (in CDCl$_3$) and the elementary analysis confirm the chemical structure of the coupling component.

Further compounds can be prepared analogously, for example: 2-Methoxy-5-isovalerylamido-N,N-dibutyl-aniline (yield: 80%) (melting point 88°–90° C. (from acetonitrile)), 3-isovalerylamido-N,N-dihexyl-aniline (yield: 89%) (melting point 38°–40° C.), 3-isovalerylamido-N-decyl-aniline (yield: 30%) (melting point 58°–60° C. (from 3:1 hexane/toluene)), 3-isovalerylamido-N-dodecyl-aniline (yield: 56%) (melting point 71°–73° C. (from 9:1 hexane/toluene)) and 2-methoxy-5-isovalerylamido-N-decyl-aniline (yield: 44%) (melting point 68°–70° C. (from 7:3 hexane/toluene)).

EXAMPLE 10

Preparation of the coupling component of the formula

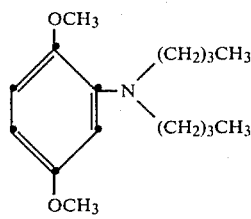

15.3 g (0.1 m) of 2,5-dimethoxy-aniline, 54.8 g (0.4 m) of butyl bromide, 20.0 g (0.5 m) of magnesium oxide and 260 ml of N,N-dimethylacetamide are kept under nitrogen at 130° C. for 6 hours. The reaction mixture is cooled and the precipitate is filtered off with suction. The filtrate is poured into 600 ml of ice water. The oily product is extracted with ether. The organic phase is washed three times with water and dried with magnesium sulfate. The solvent is evaporated off and the residue is distilled in vacuo.

This gives 19.7 g (74.3%) of N,N-dibutyl-2,5-dimethoxyaniline (boiling point 114°–118° C./0.17 mm Hg).

The nuclear magnetic resonance spectrum (in CDCl$_3$) and the elementary analysis confirm the chemical structure of the coupling component.

EXAMPLE 11

Preparation of the coupling component of the formula

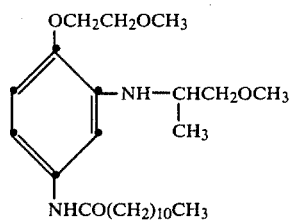

(a) 23.8 g (0.1 m) of 3-amino-4-(2-methoxy-ethoxy)-propionanilide (prepared according to European Patent Specification No. 0,011,048) are condensed with 18.9 g (0.15 m) of methoxyacetone and, at the same time, reduced with hydrogen in the presence of a hydrogenation catalyst (platinum-on-carbon). 28.4 g of 2-(2-methoxy-ethoxy)-5-propionamido-N-(2-methoxy-isopropyl)-aniline are obtained in 91% yield.

(b) 9 g of 2-(2-methoxy-ethoxy)-5-propionamido-N-(2-methoxy-isopropyl)-aniline are heated in 100 ml of a mixture of methanol and concentrated hydrochloric acid. The solution is stirred into water and neutralised with 55 ml of 30% sodium hydroxide solution. The oily layer is extracted with chloroform. The extract is dried over potassium carbonate and the solvent is evaporated off completely. The residue is dissolved in 100 ml of dioxane. 1.5 g of potassium carbonate and, finally, 6.7 g of lauric acid chloride are added to this solution. The reaction mixture is stirred for 3 hours, boiled under reflux and filtered hot. On cooling, the product precipitates, and it is filtered off with suction. The precipitate is recrystallised from ethyl acetate. This gives 6.3 g of 2-(2-methoxy-ethoxy)-5-laurylamido-N-(2-methoxy-isopropyl)-aniline in a 50% yield (melting point 148°–151° C.).

The nuclear magnetic resonance spectrum (in CDCl$_3$) and the elementary analysis confirm the chemical structure of the coupling component.

EXAMPLE 12

Preparation of the coupling component of the formula

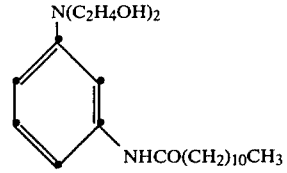

(a) 20 g (0.145 m) of 3-nitro-aniline are dissolved in 180 ml of dry dioxane, and 17.4 g (0.174 m) of calcium carbonate are added to the solution. At 15° C., 35 g (0.16 m) of lauric acid chloride in 20 ml of dioxane are then added dropwise. The suspension is stirred for two hours at room temperature and is then filtered with suction. The solid residue is extracted with 100 ml of dioxane and the organic solution obtained is evaporated to dryness. The product is dried in vacuo at 50° C.

This gives 45.8 g (98.5%) of 3-nitro-laurylanilide (melting point 69°–70° C.).

(b) 45.5 g (0.142 m) of 3-nitro-laurylanilide are dissolved in 250 ml of 2-methoxy-ethanol, 2 g of a 10% hydrogenation catalyst (palladium-on-carbon) are added and the mixture is subjected to hydrogenation under normal pressure. After the reaction has ended, the mixture is heated to 90° C. and the catalyst is filtered off hot, under nitrogen. The mixture is cooled down and the product precipitates. The precipitate is filtered off with suction and dried.

This gives 38.6 g (93.5%) of 3-amino-laurylanilide (melting point 90°–91° C.).

(c) 2.9 g (0.01 m) of 3-amino-laurylanilide and 0.9 g (0.021 m) of ethylene oxide in 25 ml of xylene are heated overnight at 140° C. in a pressure tube. The hot mixture is filtered and then cooled at 0° C. The precipitate is filtered off with suction and dried.

This gives 2.25 g (60%) of 3-N,N-bis-(hydroxyethyl)amino-laurylanilide (melting point 96°–98° C.).

The nuclear magnetic resonance spectrum (in $CDCl_3$) and the elementary analysis confirm the chemical structure of the coupling component.

EXAMPLE 13

75.9 mg of the triazene of the formula

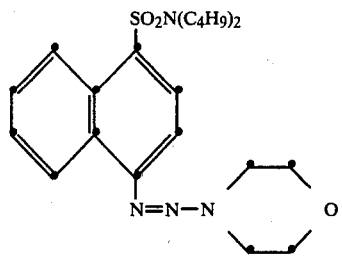

and 63.6 mg of the coupler of the formula

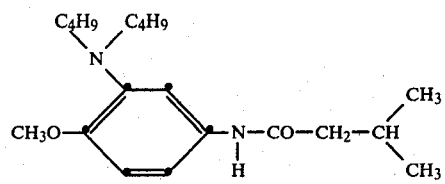

are dissolved in 3 ml of a mixture of 9 parts by weight of ethyl acetate and 1 part by weight of tricresyl phosphate. This oily solution is introduced, with stirring, into a mixture of 10.3 ml of 6% gelatine solution and 2.0 ml of a 3% aqueous solution of dibutylnaphthalenesulfonic acid (Nekal BX). The oily solution is finely emulsified in the aqueous mixture by means of an ultrasonic treatment.

2.5 ml of this emulsion are then mixed with 1.7 ml of an aqueous gelatine solution, 5 ml of water, 0.8 ml of a silver bromoiodide emulsion, which contains 22 g of silver per kg and 1 ml of a 1% solution of the compound

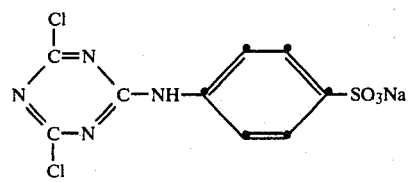

The mixture is coated in an even layer onto an opaque cellulose triacetate base, in such a way that, after drying of the layer, there are 0.12 micromol each of coupler and triazene and 0.7 micromol of silver per $cm^2$.

The dried material is exposed behind a step wedge and is then processed further at a temperature of 32° C., as follows:

| | | |
|---|---|---|
| 1. | Development: 1.5 minutes | |
| | Hydroquinone | 6.0 g |
| | Phenidone (1-phenyl-pyrazolidin-3-one) | 0.25 g |
| | Potassium sulfite | 50 g |
| | Ethylenediamine-tetraacetic acid (Na salt) | 2 g |
| | Sodium metaborate | 7.1 g |
| | Potassium bromide | 1.0 g |
| | Benzotriazole | 0.1 g |
| | Water, to make up to | 1 liter |
| 2. | Washing: 0.5 minute | |
| 3. | Combined dye formation, dye and silver bleaching: 6 minutes | |
| | Trichloroacetic acid | 70 g |
| | Sulfuric acid 98% | 15.5 g |
| | Ascorbic acid | 0.30 g |
| | Sodium iodide | 2.8 g |
| | 4-Nitrophenol-2-sulfonic acid | 1.8 g |
| | 6-Methoxy-2,3-dimethylquinoxaline | 0.3 g |
| | Water to make up to | 1 liter |
| 4. | Washing: 0.5 minute | |
| 5. | Fixing: 4 minutes | |
| | Ammonium thiosulfate | 200 g |
| | Potassium metabisulfite | 25 g |
| | Potassium hydroxide 85% | 11 g |
| | Water, to make up to | 1 liter |
| 6. | Washing: 4 minutes | |

After drying, a magenta wedge positive having a minimum density of 0.02 and a maximum density of 2.25 ($\lambda_{max.}=540$ nm) is obtained.

EXAMPLE 14

The procedure described in Example 13 is repeated, except that 44.5 mg of the triazene of the formula

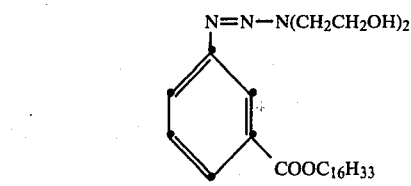

and 46.5 mg of the coupling component of the formula

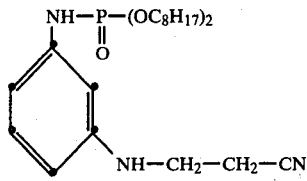

are used. The preparation of the solution in the ethyl acetate/tricresyl phosphate mixture and the emulsification in gelatine solution are carried out as in Example 13.

To prepare the coating solution, gelatine solution and silver halide emulsion are used in the same quantitative ratios as in Example 13. After a cellulose triacetate base has been coated and dried, as in Example 13, a layer is obtained which contains 0.065 micromol each of triazene and coupling component and 0.7 micromol of silver per cm².

The dried material is exposed behind a step wedge and is then processed at a temperature of 32° C., as follows:

| 1. | Development: 1.5 minutes | |
| | As in Example 13 | |
| 2. | Washing: 0.5 minute | |
| 3. | Dye formation: 6 minutes | |
| | Perchloric acid 0.5 molar = 50 g/liter | |
| 4. | Combined dye and silver bleaching: 5 minutes | |
| | Sulfuric acid 98% | 51.5 g |
| | Sodium iodide | 9.0 g |
| | 4-Nitro-2-phenolsulfonic acid (disodium salt) | 6.0 g |
| | 6-Methoxy-2,3-dimethylquinoxaline | 1.0 g |
| | Ascorbic acid | 1.0 g |
| | Water, to make up to | 1 liter |
| 5. | Washing: 0.5 minute | |
| 6. | Fixing bath: 4 minutes | |
| | As in Example 13 | |
| 7. | Washing: 4 minutes | |

A brilliant yellow positive copy of the wedge, having a minimum density of 0.03 and a maximum density of 1.05 ($\lambda_{max.}$=437 nm) is obtained.

A similar result is obtained when the dye formation and the dye bleach and silver bleach are carried out in one and the same bath, as in Example 13.

EXAMPLE 15

In accordance with Example 13, a base is provided with a layer of the following composition:

| Triazene according to Example 14 | 0.432 mmol/m² |
| --- | --- |
| Coupling component of the formula | 0.432 mmol/m² |

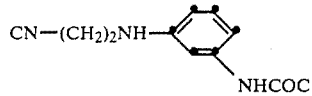

| Silver bromoiodide having a silver content of | 2.200 mmol/m² |
| --- | --- |
| Tricresyl phosphate | 0.715 g/m² |
| Gelatine | 2.015 g/m² |

This material is exposed with blue light (20 lux-seconds) behind a step wedge and is processed at 32° C. as follows:

| 1. | Development 1 minute | |
| | Composition of the developer bath as in Example 13 | |
| 2. | Washing 0.5 minute | |
| 3. | Combined dye formation, dye and silver bleaching and fixing: 3 minutes | |
| | Sulfuric acid (98%) | 15.5 g |
| | Sodium iodide | 2.7 g |
| | 6-Methoxy-2,3-dimethyl-quinoxaline | 0.3 g |
| | Thiourea | 75.0 g |
| | Ascorbic acid | 1.0 g |
| | Trichloroacetic acid | 70.0 g |
| | Water, to make up to | 1 liter |
| 4. | Washing 3 minutes | |

After drying, a yellow wedge positive having a minimum density of 0.02, a blue reflection density of 1.50 and a residual silver content of less than 0.005 g/m² is obtained.

EXAMPLE 16

A photographic multi-layer material (tripack) is prepared by successively applying the following layers to a triacetate base:

(a) a red-sensitive silver bromide emulsion layer having a coating weight of 2 g/m² of gelatine, 0.5 g/m² of silver and 112 mg/m² of the cyan dye of the formula

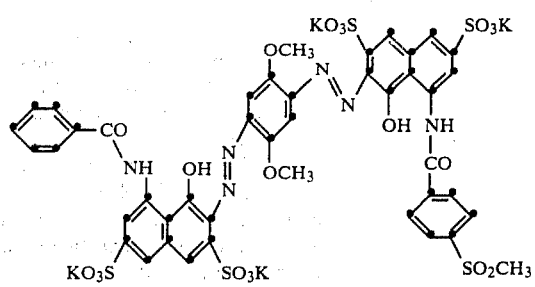

(b) a gelatine interlayer having a coated weight of 2.5 g/m², (c) a green-sensitive layer according to Example 13, (d) a gelatine interlayer according to (b), (e) a blue-sensitive layer according to Example 15, in which, however, the content of silver, triazene and coupling component is increased by a factor of 1.33, and (f) a gelatine protective layer having a coating weight of 1.25 g/m².

The dried material is exposed through a step wedge with blue (20.0 Lux.sec), green (20.0 Lux.sec) and red light (30.0 Lux.sec) and processed as described under Example 13. A well balanced grey wedge with a maximum density of 2.1 and a minimum density of 0.05 is obtained.

What is claimed is:

1. A photographic material for the production of photographic colour images by the silver dye bleach process, which process comprises the steps of imagewise exposure, silver development, dye formation, dye bleach, silver bleach and fixing of the photographic material and wherein said process steps, after the development of the image silver are carried out in acid processing solution which contains a phase transfer catalyst capable of transferring cations said photographic material comprising an opaque or transparent base, having thereon at least one silver halide emulsion layer and, in the same layer or in an adjacent layer, containing a dispersion of the oil-soluble triazine of the formula

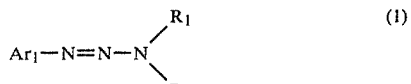

or

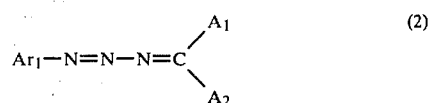

and an oil-soluble coupling component of the formula

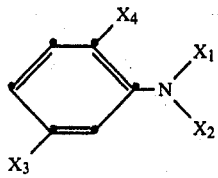
(3)

in a water-insoluble solvent or solvent mixture in which $Ar_1$ is substituted or unsubstituted aryl or a substituted or unsubstituted aromatic heterocyclic radical, $R_1$ is hydrogen, substituted or unsubstituted alkyl having 1 to 6 carbon atoms, $-(CH_2CH_2O)_r-L_1$ or $-OL_1$, in which $L_1$ is alkyl having 1 to 12 carbon atoms and r is 1, 2 or 3, or $R_1$ is substituted or unsubstituted aryl, hydroxyl or a radical of the formula

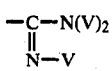

in which V is hydrogen or alkyl having 1 to 12 carbon atoms, $R_2$ is substituted or unsubstituted alkyl having 1 to 6 carbon atoms, $-(CH_2CH_2O)_r-L_1$, with $L_1$ and r being as defined above, or substituted or unsubstituted aryl, or $R_1$ and $R_2$, conjointly with the nitrogen atoms to which they are bonded, form a substituted or unsubstituted, saturated or unsaturated 5-membered, 6-membered or 7-membered ring which may contain a further hetero-atom, $A_1$ and $A_2$ independently of one another are an amino group of the formula

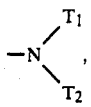

in which $T_1$ and $T_2$ independently of one another are hydrogen, substituted or unsubstituted alkyl having 1 to 12 carbon atoms or substituted or unsubstituted aryl, $X_1$ and $X_2$ independently of one another are hydrogen or substituted or unsubstituted alkyl having 1 to 20 carbon atoms, $X_3$ is hydrogen, substituted or unsubstituted alkyl having 1 to 6 carbon atoms, substituted or unsubstituted alkoxy having 1 to 20 carbon atoms, $-O(C_2H_4O)_n-H$, $-O(CH_2)_m-OH$, $-O-(CH_2)_m-OZ_1$ or $-O-(C_2H_4O)_n-Z_1$, in which $Z_1$ is alkyl having 1 to 8 carbon atoms, n is an integer from 1 to 5, and m is 2, 3 or 4, or $X_3$ is substituted or unsubstituted aryloxy, hydroxyl, halogen, $-NHCO-Y_1$, $-NHCOH$, $-NHCO-OY_1$, $-NHP(O)(OY_1)_2$ or $-NHSO_2-Y_1$, in which $Y_1$ is substituted or unsubstituted alkyl having 1 to 16 carbon atoms, $-O(CH_2)_m-OH$, $-O-(C_2H_4O)_n-H$, $-O-(CH_2)_m-OZ_1$ or $-O-(C_2H_4O)_n-Z_1$, with $Z_1$, m and n being as defined above, or $Y_1$ is substituted or unsubstituted aryl, and $X_4$ is hydrogen, substituted or unsubstituted alkyl having 1 to 12 carbon atoms, $-O(C_2H_4O)_n-H$, $-O(CH_2)_m-OH$, $-O(CH_2)_m-OZ_1$ or $-O-(C_2H_4O)_n-Z_1$, m and n being as defined above, or $X_4$ is substituted or unsubstituted alkoxy having 1 to 16 carbon atoms, substituted or unsubstituted aryloxy or halogen, and the total of the carbon atoms in the substituents $X_1$, $X_2$, $X_3$ and $X_4$ is at least 10.

2. A process for the production of a photographic colour image by the silver dye bleach process, which process comprises imagewise exposure, silver development, dye formation, dye bleaching, silver bleaching and fixing of the photographic material, said photographic material being one of claim 1, and wherein said process steps, after the development of the image silver are carried out in an acid processing solution which contains a phase transfer catalyst capable of transferring cations.

3. A process according to claim 2, wherein the triazene is of the formula

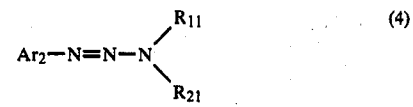

or

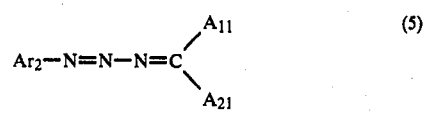

and the oil-soluble coupling component is of the formula

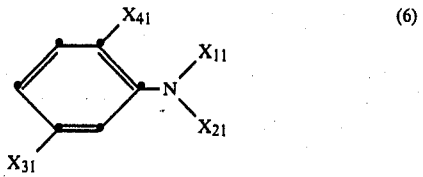

in which $Ar_2$ is substituted or unsubstituted phenyl, substituted or unsubstituted naphthyl or a substituted or unsubstituted, aromatic radical containing 1 to 3 heteroatoms, $R_{11}$ is substituted or unsubstituted alkyl having 1 to 6 carbon atoms, $-(CH_2CH_2O)_r-L_{11}$ or $-OL_{11}$, in which $L_{11}$ is alkyl having 1 to 8 carbon atoms and r is 1, 2 or 3, or is substituted or unsubstituted phenyl, or hydroxyl, $R_{21}$ is substituted or unsubstituted alkyl having 1 to 6 carbon atoms, $-(CH_2CH_2O)_r-L_{11}$, with $L_{11}$ and r being as defined above, or is substituted or unsubstituted phenyl, or $R_{21}$ and $R_{11}$, conjointly with the nitrogen atom to which they are bonded, form a substituted or unsubstituted, saturated or unsaturated 5-membered, 6-membered or 7-membered ring which may contain a further hetero-atom, $A_{11}$ and $A_{21}$ independently of one another are an amino group of the formula

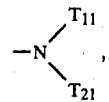

in which $T_{11}$ and $T_{21}$ independently of one another are hydrogen, alkyl having 1 to 12 carbon atoms or phenyl, $X_{11}$ and $X_{21}$ independently of one another are hydrogen or substituted or unsubstituted alkyl having 1 to 16 carbon atoms, $X_{31}$ is hydrogen, substituted or unsubstituted alkyl having 1 to 4 carbon atoms, substituted or unsubstituted alkoxy having 1 to 16 carbon atoms, $-O(C_2H_4O)_n-H$, $-O(CH_2)_m-OH$, $-O(CH_2)_m-OZ_{11}$ or $-O-(C_2H_4O)_n-Z_{11}$, in which $Z_{11}$ is alkyl having 1 to 4 carbon atoms and m and n are as defined in claim 1, or $X_{31}$ is substituted or unsubstituted phenoxy, hydroxyl, halogen, $-NHCO-Y_2$, $-NHCO-OY_2$, $-NHCOH$, $-NHP(O)(OY_2)_2$ or $-NH$-

SO₂—Y₂, in which Y₂ is substituted or unsubstituted alkyl having 1 to 16 carbon atoms, —(C₂H₄O)ₙ—H, —(CH₂)ₘ—OH, —(CH₂)ₘ—OZ₁₁ or —(C₂H₄O)ₙ—Z₁₁, with Z₁₁, n and m being as defined above, or Y₂ is substituted or unsubstituted phenyl, and X₄₁ is hydrogen, substituted or unsubstituted alkyl having 1 to 8 carbon atoms, —O(C₂H₄O)ₙ—H, —O(CH₂)ₘ—OH, —O(CH₂)ₘ—OZ₁₁ or —O—(C₂H₄O)ₙ—Z₁₁, with Z₁₁, m and n being as defined above, or X₄₁ is substituted or unsubstituted alkoxy having 1 to 16 carbon atoms, substituted or unsubstituted phenoxy or halogen, the total of the carbon atoms in the substituents X₁₁, X₂₁, X₃₁ and X₄₁ being at least 10.

4. A process according to claim 2, wherein the triazene is of the formula

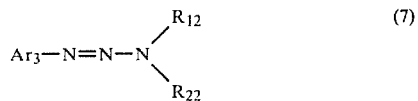

and the oil-soluble coupling component is of the formula

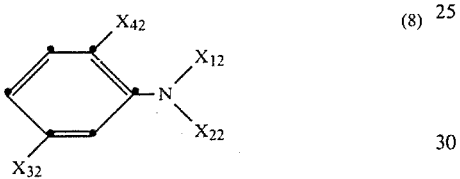

in which Ar₃ is substituted or unsubstituted phenyl or substituted or unsubstituted naphthyl, R₁₂ is alkyl having 1 to 6 carbon atoms, which is unsubstituted or substituted by hydroxyl, cyano, methoxy, carboxyl, carbalkoxy having 2 to 7 carbon atoms, in which the alkoxy moiety can be further substituted, or by —SO₃M, in which M is hydrogen, ammonium or an alkali metal, or R₁₂ is —(CH₂CH₂O)ᵣ—L₁₁ or —OL₁₁, in which L₁₁ and r are as defined in claim 3, or phenyl which is unsubstituted or substituted by alkyl having 1 to 6 carbon atoms or by halogen or alkoxy or is hydroxyl, R₂₂ is alkyl having 1 to 6 carbon atoms, which is unsubstituted or substituted by hydroxyl, cyano, methoxy, carboxyl, carbalkoxy having 2 to 7 carbon atoms, in which the alkoxy moiety can be further substituted, or by —SO₃M, in which M is hydrogen, ammonium or an alkali metal, or R₂₂ is —(CH₂CH₂O)ᵣ—L₁₁, in which L₁₁ and r are as defined in claim 3, or phenyl which is unsubstituted or substituted by alkyl having 1 to 6 carbon atoms or halogen, or R₂₂ and R₁₂, conjointly with the nitrogen atom to which they are bonded, form a saturated or unsaturated 5-membered, 6-membered or 7-membered ring which is unsubstituted or substituted by alkyl having 1 to 6 carbon atoms and may contain a nitrogen atom or oxygen atom as a further heteroatom, X₁₂ and X₂₂ independently of one another are hydrogen, alkyl having 1 to 16 carbon atoms, benzyl, phenylethyl or a radical of the formula —CHM₁—CH₂M₂, in which M₁ is hydrogen or alkyl having 1 to 4 carbon atoms and M₂ is cyano or a radical of the formula —OM₃ or —CO₂M₃, in which M₃ is hydrogen, alkyl having 1 to 16 carbon atoms, phenyl which is unsubstituted or substituted by alkyl having 1 to 4 carbon atoms, or a radical of the formula —(C₂H₄O)ₙM₄ or —(CH₂)ₘOM₄, in which M₄ is hydrogen or substituted or unsubstituted alkyl having 1 to 4 carbon atoms, and n and m are as defined above, X₃₂ is hydrogen, alkyl having 1 to 4 carbon atoms, alkoxy having 1 to 16 carbon atoms, —O(C₂H₄O)ₙ—H, —O(CH₂)ₘ—OH, —O(C₂H₄O)ₘ—Z₁₁ or —O(CH)₂)ₘ—OZ₁₁, in which Z₁₁ is as defined in claim 3 and n and m are as defined above, or X₃₂ is phenoxy, hydroxyl, halogen, —NHCO—Y₃, —NHCOH, —NHCO—OY₃, —NHP(O)(OY₃)₂ or —NHSO₂—Y₃, in which Y₃ is alkyl having 1 to 16 carbon atoms, phenyl which is unsubstituted or substituted by alkyl having 1 to 4 carbon atoms or is a radical of the formula —(C₂H₄O)ₙ—H, —(CH₂)ₘ—OH, —(C₂H₄O)ₘZ₁₁ or —(CH₂)ₘOZ₁₁, with Z₁₁, n and m being as defined above, and X₄₂ is hydrogen, alkyl having 1 to 6 carbon atoms, halogen, alkoxy having 1 to 8 carbon atoms, or —O(C₂H₄O)ₙ—H, —O(CH₂)ₘ—OH, —O(CH₂)ₘ—OZ₁₁ or —O(C₂H₄O)ₙ—Z₁₁, with Z₁₁, n and m being as defined above, or X₄₂ is substituted or unsubstituted phenoxy, the total of the carbon atoms in the substitutents X₁₂, X₂₂, X₃₂ and X₄₂ being at least 10.

5. A process according to claim 4, wherein the oil-soluble coupling component is of the formula (8) and the triazene is of the formula

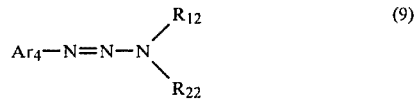

in which Ar₄ is of the formula

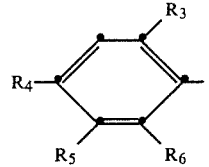

in which R₃ and R₆ independently of one another are hydrogen, substituted or unsubstituted alkyl or alkoxy each having 1 to 4 carbon atoms, carboxyl, carbalkoxy having 2 to 12 carbon atoms, —SO₂T₁, —SO₂N(T₁) or —SO₂NT₁T₂, in which T₁ and T₂ are as defined in claim 1, halogen, cyano or nitro, R₄ is hydrogen, substituted or unsubstituted alkyl or alkoxy each having 1 to 20 carbon atoms, carbalkoxy having 2 to 21 carbon atoms, in which the alkoxy moiety can be further substituted, —SO₂T₃, —SO₂N(T₃)₂ or —SO₂NT₁T₃, in which T₃ is alkyl having 1 to 20 carbon atoms or —(CH₂)ₚ—OT₁, T₁ is as defined above and p is 2, 3 or 4, or R₄ is halogen, trifluoromethyl, cyano, nitro or a radical of the formula

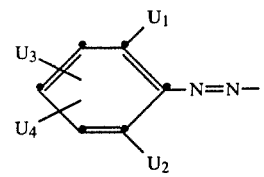

in which U₁ and U₂ independently of one another are hydrogen, —SO₂U₅, in which U₅ is alkyl having 1 to 4 carbon atoms, or are halogen, cyano or nitro, U₃ is hydrogen, halogen or nitro and U₄ is substituted or unsubstituted alkyl or alkoxy each having 1 to 20 carbon atoms, —SO₂T₃, —SO₂NTT₃, in which T₁ and T₃ are as defined above, or carbalkoxy having 2 to 21 carbon atoms, in which the alkoxy moiety can be further substituted, R₅ is hydrogen, substituted or unsubstituted alkyl or alkoxy each having 1 to 20 carbon atoms, carbalkoxy having 2 to 21 carbon atoms, in which the alkoxy moiety can be further substituted, —SO₂T₃, —SO₂N(T₃)₂ or —SO₂NT₁T₃, in which T₁ and T₃ are as defined above, or R₅ conjointly with R₄ forms a radical of the formula

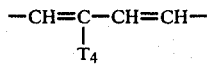

or R₅ conjointly with R₆ forms a radical of the formula

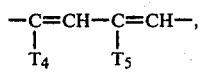

in which T₄ is hydrogen, nitro, —SO₂T₃, —SO₂N(T₃)₂ or —SO₂NT₁T₃ and T₅ is hydrogen, —OT₃, —SO₂T₃ or —SO₂NT₁T₃, T₁ and T₃ being as defined above, the total of the carbon atoms in the substituents R₃, R₄, R₅ and R₆ being at least 8, and R₁₂, R₂₂ as well as X₁₂, X₂₂, X₃₂ and X₄₂ being as defined in claim 4.

6. A process according to claim 5, wherein the oil-soluble coupling component is of the formula (8) and the triazene is of the formula

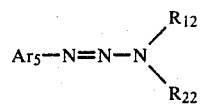 (10)

in which Ar₅ is of the formula

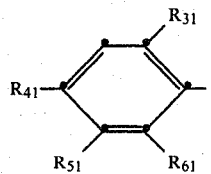

in which R₃₁ and R₆₁ independently of one another are hydrogen, alkyl or alkoxy each having 1 or 2 carbon atoms, trifluoromethyl, carboxyl, carbalkoxy having 2 to 7 carbon atoms, —SO₂T₁₁, —SO₂N(T₁₁)₂ or —SO₂NT₁₁T₂₁, in which T₁₁ and T₂₁ are as defined in claim 3, or are fluorine, chlorine, bromine, cyano or nitro, R₄₁ is hydrogen, alkyl having 1 to 20 carbon atoms, trifluoromethyl, alkoxy having 1 to 20 carbon atoms, which is unsubstituted or substituted by alkoxy having 1 to 6 carbon atoms, or is carbalkoxy having 2 to 21 carbon atoms, in which the alkoxy moiety is unsubstituted or substituted further by alkoxy having 1 to 6 carbon atoms, or is —SO₂T₃₁, —SO₂N(T₃₁)₂ or —SO₂NT₁₁T₃₁, in which T₃₁ is alkyl having 1 to 20 carbon atoms or —(CH₂)ₚ—OT₁₁, in which T₁₁ is as defined above and p is 2, 3 or 4, or R₄ is chlorine, bromine, cyano, nitro or a radical of the formula

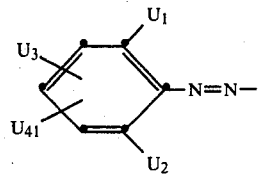

in which U₄₁ is hydrogen, alkyl having 1 to 20 carbon atoms, trifluoromethyl, alkoxy having 1 to 20 carbon atoms, which is unsubstituted or substituted by alkoxy having 1 to 6 carbon atoms, or is —SO₂T₃₁, —SO₂NT₁₁T₃₁, in which T₁₁ and T₃₁ are as defined above, or is carbalkoxy having 2 to 21 carbon atoms in which the alkoxy moiety is unsubstituted or further substituted by alkoxy having 1 to 6 carbon atoms, R₅₁ is hydrogen, alkyl having 1 to 20 carbon atoms, alkoxy having 1 to 20 carbon atoms, which is unsubstituted or substituted by alkoxy having 1 to 12 carbon atoms or by hydroxyl, or is carbalkoxy having 2 to 21 carbon atoms, in which the alkoxy moiety is unsubstituted or substituted by alkoxy having 1 to 12 carbon atoms, or is —SO₂T₃₁, —SO₂N(T₃₁)₂ or —SO₂NT₁₁T₃₁, in which T₁₁ and T₃₁ are as defined above, or R₅₁ conjointly with R₄₁ forms a radical of the formula

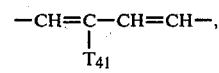

or R₅₁ conjointly with R₆₁ forms a radical of the formula

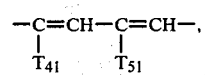

in which T₄₁ is hydrogen, nitro, —SO₂T₃₁, —SO₂N(T₃₁)₂ or —SO₂NT₁₁T₃₁ and T₅₁ is hydrogen, —OT₃₁, —SO₂T₃₁ or —SO₂NT₁₁T₃₁, in which T₁₁ and T₃₁ are as defined above, the total of the carbon atoms in the substituents R₃₁, R₄₁, R₅₁ and R₆₁ being at least 10, and R₁₂, R₂₂ as well as U₁, U₂ and U₃ being as defined in claim 5.

7. A process according to claim 6, wherein the triazene is of the formula (10) and the oil-soluble coupling component is of the formula

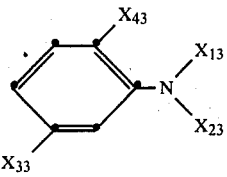 (11)

in which X₁₃ is alkyl having 1 to 16 carbon atoms or a radical of the formula —CHM₁—CH₂M₂, in which M₁ and M₂ are as defined in claim 4, X₂₃ is hydrogen, alkyl having 1 to 16 carbon atoms, a radical of the formula —CHM₁—CH₂M₂, in which M₁ and M₂ are as defined above, or is benzyl or phenylethyl, X₃₃ is hydrogen, alkyl having 1 to 4 carbon atoms, alkoxy having 1 to 12 carbon atoms, —O(C₂H₄O)ₙ—Z₁₁ or —O(CH₂)ₘ—OZ₁₁, in which Z₁₁, n and m are as defined in claim 4, or is phenoxy, hydroxyl, chlorine, bromine, —NHCO—Y₃, —NHCOH, —NHCO—OY₃, —NHP(O)-

$(OY_3)_2$ or $-NHSO_2-Y_3$, in which $Y_3$ is as defined in claim 4, and $X_{43}$ is hydrogen, alkyl having 1 to 4 carbon atoms, chlorine, bromine, alkoxy having 1 to 8 carbon atoms or $-O-(CH_2CH_2O)_n-Z_{11}$, in which $Z_{11}$ and n are as defined above, the total of the carbon atoms in the substituents $X_{13}$, $X_{23}$, $X_{33}$ and $X_{43}$ being at least 10.

8. A process according to claim 7, wherein the triazene is of the formula

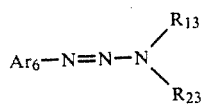
(12)

and the oil-soluble coupling component is of the formula

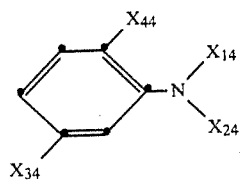
(13)

in which $Ar_6$ is of the formula

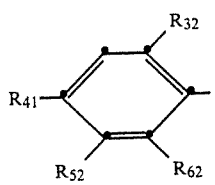

in which $R_{32}$ and $R_{62}$ independently of one another are hydrogen, methyl, methoxy, trifluoromethyl, carbalkoxy having 2 to 4 carbon atoms, $-SO_2T_{13}$, $-SO_2N(T_{13})_2$ or $-SO_2NT_{13}T_{23}$, in which $T_{13}$ and $T_{23}$ independently of one another are hydrogen or alkyl having 1 or 2 carbon atoms, or $R_{32}$ and $R_{62}$ are fluorine, chlorine, bromine, cyano or nitro, $R_{52}$ is hydrogen, alkyl having 1 to 20 carbon atoms, $-OT_{31}$, $-CO-OT_{31}$ or $-SO_2T_{31}$, in which $T_{31}$ is as defined in claim 6 or $R_{52}$ conjointly with $R_{41}$ forms a radical of the formula

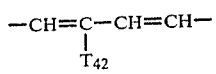

or $R_{52}$ conjointly with $R_{62}$ forms a radical of the formula

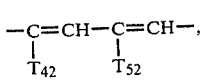

in which $T_{42}$ is hydrogen, nitro, $-SO_2T_{32}$ or $-SO_2N(T_{32})_2$ and $T_{52}$ is hydrogen, $-OT_{32}$, $-SO_2T_{32}$, or $-SO_2NT_{12}T_{32}$, in which $T_{32}$ is alkyl having 1 to 10 carbon atoms or $-(CH_2)_p-OT_{12}$ and p and $T_{12}$ as well as $R_{41}$ are as defined in claim 6, the total of the carbon atoms in the substituents $R_{32}$, $R_{41}$, $R_{52}$ and $R_{62}$ being at least 10, $R_{13}$ is alkyl having 1 to 4 carbon atoms, alkyl having 1 or 2 carbon atoms, which is unsubstituted or substituted by hydroxyl, cyano, carboxyl, $-COOCH_3$ or methoxy, or is $-(CH_2CH_2O)_r-L_{12}$ or $-OL_{12}$, in which $L_{12}$ is alkyl having 1 to 6 carbon atoms and r is as defined in claim 3, or $R_{13}$ is phenyl, tolyl, chlorophenyl, bromophenyl or methoxyphenyl, $R_{23}$ is alkyl having 1 to 4 carbon atoms, alkyl having 1 or 2 carbon atoms, which is unsubstituted or substituted by hydroxyl, cyano, carboxyl, $-COOCH_3$ or methoxy, or is $-(CH_2CH_2O)_r-L_{12}$, in which $L_{12}$ and r are as defined above, or $R_{23}$ is phenyl, tolyl, chlorophenyl or bromophenyl, or $R_{23}$ and $R_{13}$ form a radical of the formula $-(CH_2)_4-$, $-(CH_2)_5-$, $-C_2H_4-O-C_2H_4-$, $-C_2H_4-NH-C_2H_4-$, $-C_2H_4-N(CH_3)-C_2H_4-$, $-CH=N-CH=CH-$ or $-CH=CH-CH=CH-$, and $X_{14}$ is alkyl having 1 to 16 carbon atoms or a radical of the formula $-CHM_{11}-CH_2M_{21}$, in which $M_{11}$ is hydrogen, methyl or ethyl and $M_{21}$ is cyano or $-OM_{31}$, in which $M_{31}$ is hydrogen, alkyl having 1 to 6 carbon atoms or phenyl which is unsubstituted or substituted by alkyl having 1 to 4 carbon atoms, $X_{24}$ is hydrogen, alkyl having 1 to 16 carbon atoms or benzyl, $X_{34}$ is hydrogen, alkyl having 1 to 4 carbon atoms, phenoxy, chlorine, hydroxyl, alkoxy having 1 to 6 carbon atoms, $-O-CH_2CH_2-OH$, $-O-CH_2CH_2-OZ_{11}$, $-NHCO-Y_4$, $-NHCOH$, $-NHCO-CH_2CH_2-OH$, $-NHCO-CH_2CH_2-OZ_{11}-NHP(O)(OY_4)_2$, $-NHP(O)(OC_6H_4Y_5)_2$ or $-NHSO_2Y_4$, in which $Y_4$ is alkyl having 1 to 16 carbon atoms, $Y_5$ is hydrogen or alkyl having 1 to 6 carbon atoms and $Z_{11}$ is as defined in claim 7, and $X_{44}$ is hydrogen, alkyl or alkoxy each having 1 to 4 carbon atoms or $-O-(CH_2CH_2O)_n-Z_{11}$, in which $Z_{11}$ and n are as defined in claim 7, the total of the carbon atoms in the substituents $X_{14}$, $X_{24}$, $X_{34}$ and $X_{44}$ being at least 10.

9. A process according to claim 4, wherein the oil-soluble coupling compound is of the formula (8) and the triazene is of the formula

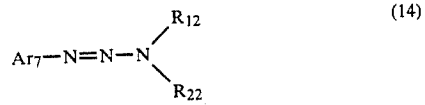
(14)

in which $Ar_7$ is a substituted or unsubstituted, aromatic 5-membered or a 6-membered radical which contains 1 to 3 oxygen, sulfur and/or nitrogen atoms and $R_{12}$ and $R_{22}$ are as defined in claim 4.

10. A process according to claim 9, wherein the oil-soluble coupling compound is of the formula (8) and the triazene is of the formula

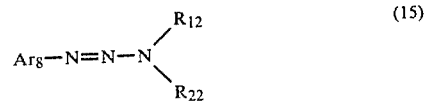
(15)

in which $Ar_8$ is a radical of the formula

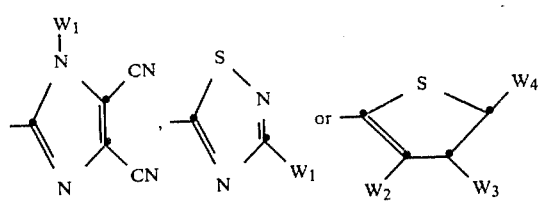

in which $W_1$ is substituted or unsubstituted alkyl having 6 to 18 carbon atoms or substituted or unsubstituted phenyl, $W_2$ is carbalkoxy having 2 to 25 carbon atoms, nitro or cyano, and $W_3$ and $W_4$ independently of one another are hydrogen or alkyl having 1 to 6 carbon atoms, or $W_3$ conjointly with $W_4$ forms a radical of the formula

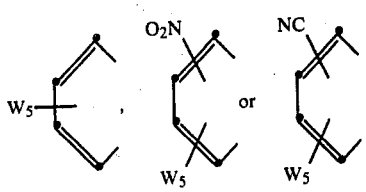

in which $W_5$ is alkyl having 6 to 18 carbon atoms, the total of the carbon atoms in the substituents $W_1$, $W_2$, $W_3$ and $W_4$ being at least 8, and $R_{12}$ and $R_{22}$ being as defined in claim 9.

11. A process according to claim 10, wherein the triazene is of the formula (15) and the oil-soluble coupling component is of the formula (11).

12. A process according to claim 11, wherein the oil-soluble coupling component is of the formula (13) and the triazene is of the formula

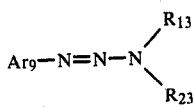

(16)

in which $Ar_9$ is a radical of the formula

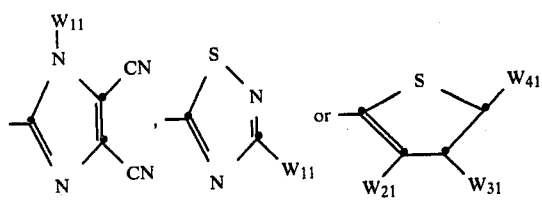

in which $W_{11}$ is alkyl having 1 to 18 carbon atoms or phenyl which is unsubstituted or substituted by alkyl or alkoxy each having 6 to 18 carbon atoms, $W_{21}$ is carbalkoxy having 2 to 19 carbon atoms, nitro or cyano, and $W_{31}$ and $W_{41}$ independently of one another are hydrogen or alkyl having 1 to 4 carbon atoms, or $W_{31}$ and $W_{41}$ conjointly form a radical of the formula

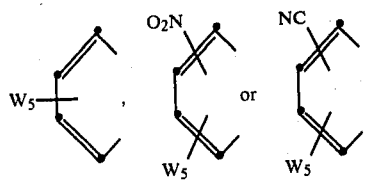

in which $W_5$ is as defined in claim 10, the total of the carbon atoms in the substituents $W_{11}$, $W_{21}$, $W_{31}$, $W_{41}$ and $W_5$ being at least 10, and $R_{13}$ and $R_{23}$ being as defined in claim 8.

13. A process according to claim 2, wherein the material, in at least one silver halide emulsion layer, or in one adjacent layer in each case, contains an oil-soluble triazene of the formula (1) or (2) and an oil-soluble coupling component of the formula (3), the triazene and the coupling component having been incorporated, in solution in a water-immiscible solvent or solvent mixture, in a finely divided form into the light-sensitive silver halide emulsion layer or layers or into a layer adjacent to the latter, and, after exposure and development of the image silver, the material is treated with an aqueous processing bath which, for dye formation, contains (a) a strong acid, (b) a cation phase transfer catalyst, optionally for a simultaneous dye bleaching (c) a ligand which forms silver complexes, (d) a dye bleach catalyst, (e) an antioxidising agent, optionally for a simultaneous silver bleaching, (f) an oxidising agent and, optionally for simultaneous fixing (g) a solvent for silver halide.

14. A process according to claim 13, wherein the aqueous processing bath contains the 7 components (a) to (g).

15. A process according to claim 13, wherein the aqueous processing bath contains the 6 components (a) to (f), and fixing is carried out in a separate processing bath.

16. A process as claimed in claim 13, wherein the aqueous processing bath contains the 5 components (a) to (e), and the silver bleach and fixing are carried out separately in one or two distinct processing baths.

17. A process according to claim 13, wherein the aqueous processing bath contains the two components (a) and (b), and the dye bleach and silver bleach and the fixing are carried out separately in one, two or three distinct processing baths.

18. A process according to claim 13, wherein the cation transfer catalyst is a strong inorganic acid, a perhalogenated aliphatic acid, a benzenesulfonic acid which is substituted by 1 or 2 alkyl or alkoxy groups each having 1 to 12 carbon atoms, a benzenesulfonic acid substituted by 1 to 3 halogen atoms, an alkyl sulfonic acid which may be halogenated, having 1 to 12 carbon atoms, a monoalkyl-sulfuric acid having 1 to 12 carbon atoms, or an alkali metal salt or ammonium salt of these acids.

19. A process according to claim 18, wherein the cation transfer catalyst is a hydrogen halide acid, a perhalogenated alkanoic acid having 1 to 6 carbon atoms, a benzenesulfonic acid which is substituted by 1 or 2 alkyl or alkoxy groups each having 1 to 8 carbon atoms, a benzenesulfonic acid which is substituted by 1 to 3 halogen atoms, an alkylsulfonic acid which may be halogenated, having 1 to 8 carbon atoms, a monoalkylsulfuric acid having 1 to 8 carbon atoms, or an alkali metal salt or ammonium salt of these acids.

20. A process according to claim 19, wherein the cation phase transfer catalyst is perchloric acid or periodic acid, hydrobromic or hydriodic acid, trifluoro-, trichloro- or tribromo-acetic acid, pentafluoro- or pentachloro-propionic acid, p-toluenesulfonic acid, p-isopropylbenzenesulfonic acid, 2,4-dimethylbenzenesulfonic acid, p-chlorobenzenesulfonic acid, 2,4-dichlorobenzenesulfonic acid, 3,4-dichlorobenzenesulfonic acid, 3,6-dichlorobenzenesulfonic acid, p-methoxybenzenesulfonic acid, p-butoxybenzenesulfonic acid, methanesulfonic acid, ethanesulfonic acid, hexanesulfonic acid, trifluoromethanesulfonic acid or trichloromethanesulfonic acid or a sodium salt, potassium salt or ammonium salt of these acids.

21. A process according to claim 20, wherein the cation phase transfer catalyst is trifluoro- or trichloroacetic acid or perchloric acid.

22. A process according to claim 13, wherein the cation phase transfer catalyst is employed in quantities of 10 to 200 g per liter of processing solution.

23. A photographic material according to claim 1, which contains, in each case in one layer, one red-sensitive, green-sensitive and blue-sensitive silver halide gelatine emulsion and, in each case in the same layer or an adjacent layer, an associated dispersion, which forms the respective complementary colour cyan, magenta or yellow, of a solution of an oil-soluble triazene of the formula (1) or (2) and a coupling component of the formula (3) in a water-immiscible solvent or solvent mixture.

24. A process according to claim 2, wherein the dye formation is carried out together with the dye bleaching, silver bleaching and fixing, or the silver-bleaching is carried out together with the dye-bleaching and/or fixing in a single processing bath.

25. A process according to claim 22, wherein said cation phase transfer catalyst is employed in quantities of 10 to 200 g per liter of processing solution.

* * * * *